US008071579B2

(12) United States Patent
Ashworth et al.

(10) Patent No.: US 8,071,579 B2
(45) Date of Patent: Dec. 6, 2011

(54) DNA DAMAGE REPAIR INHIBITORS FOR THE TREATMENT OF CANCER

(75) Inventors: Alan Ashworth, London (GB); Stephen Jackson, Cambridge (GB); Niall Martin, Cambridge (GB); Graeme Smith, Cambridge (GB)

(73) Assignees: The Institute of Cancer Research: Royal Cancer Hospital, London (GB); Kudos Pharmaceuticals Limited, Cambridge (GB)

( * ) Notice: Subject to any disclaimer, the term of this patent is extended or adjusted under 35 U.S.C. 154(b) by 985 days.

(21) Appl. No.: 11/001,474

(22) Filed: Nov. 30, 2004

(65) Prior Publication Data
US 2005/0227919 A1    Oct. 13, 2005

Related U.S. Application Data

(60) Provisional application No. 60/526,244, filed on Dec. 1, 2003.

(30) Foreign Application Priority Data

Dec. 1, 2003 (GB) .................................. 0327844.7

(51) Int. Cl.
*A61K 31/50* (2006.01)
*A61K 31/44* (2006.01)
*A61K 31/415* (2006.01)
*A61K 31/40* (2006.01)
*A01N 43/00* (2006.01)

(52) U.S. Cl. ........ 514/183; 514/248; 514/356; 514/394; 514/417

(58) Field of Classification Search .................. 514/414, 514/419; 548/492, 495
See application file for complete search history.

(56) References Cited

U.S. PATENT DOCUMENTS

| | | | |
|---|---|---|---|
| 5,484,951 A | 1/1996 | Kun et al. | |
| 5,519,053 A | 5/1996 | Kun et al. | |
| 5,652,367 A | 7/1997 | Kun et al. | |
| 5,908,861 A | 6/1999 | Kun | |
| 6,548,494 B1 | 4/2003 | Webber et al. | |
| 7,072,771 B2 | 7/2006 | Oliveira | |
| 7,087,637 B2* | 8/2006 | Grandel et al. ............. | 514/414 |
| 7,176,188 B2 | 2/2007 | Desnoyers | |
| 7,351,530 B1 | 4/2008 | Bepler | |
| 7,351,701 B2 | 4/2008 | Helleday et al. | |
| 2002/0032319 A1* | 3/2002 | Cargill et al. ............. | 536/23.1 |
| 2002/0155988 A1 | 10/2002 | O'Hare et al. | |
| 2002/0183335 A1* | 12/2002 | Hewawasam et al. ...... | 514/256 |
| 2003/0229004 A1 | 12/2003 | Zarling et al. | |
| 2006/0142231 A1 | 6/2006 | Ashworth et al. | |
| 2007/0179160 A1 | 8/2007 | Helleday | |

FOREIGN PATENT DOCUMENTS

| | | |
|---|---|---|
| EP | 0 600 831 A1 | 11/1993 |
| WO | 95/24379 | 9/1995 |
| WO | WO 95/24379 | 9/1995 |
| WO | 00/42040 | 7/2000 |
| WO | 01/16136 | 3/2001 |
| WO | 02/12239 | 2/2002 |
| WO | WO 92/12239 A1 | 2/2002 |
| WO | WO 02/36576 A1 | 5/2002 |
| WO | WO 02/090334 A1 | 11/2002 |
| WO | WO 03/014090 A1 | 2/2003 |
| WO | WO 03/063874 A1 | 8/2003 |
| WO | WO 03-070234 A1 | 8/2003 |
| WO | WO 03/093261 A1 | 11/2003 |
| WO | WO 2004/008976 A1 | 1/2004 |
| WO | 05/012524 | 2/2005 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*
Berthet et al., "DNA repair inhibitors", Expert Opinion on Therapeutic Patents,(1999) 9(4):401-415.*
Perkins et al, "Novel inhibitros of PAR . . . ", Cancer Res 61, 4175-4183, May 15, 2001.*
Calabrese et al., "Indentificatin of Potent Nontoxic PARP Inhibitors . . . ", Clin. Cancer Res., vol. 9, 2711-2178, Jul. 2003.*
Dorwald (Side Reactions in Organic Synthesis: A Guide to Successful Synthesis Design, Weinheim: Wiley-VCH Verlag GmbH & Co. KGaA, 2005, Preface).*
Schultz et al. Poly(ADP-ribose) polymerase (PARP-1) has a controlling role in homologous recombination. Nucleic Acids Research, 2003, vol. 31, No. 17, 4959-4964.*
Fan et al. Disruption of p53 function sensitizes breast cancer MCF-7 cells to cisplatin and pentoxifylline. Cancer Research, 55, 1649-1654, Apr. 15, 1995.*
Jönsson, Göran; et al., "High-Resolution Genomic Profiles of Breast Cancer Cell Lines Assessed by Tiling BAC Array Comparative Genomic Hybridization", Genes, Chromosomes and Cancer, 2007, 46:543-558.
Sanger Institute database entry for MDA_MB-231, Catalogue of Somatic Mutations in Cancer, 2 pgs.
Turner, Nicholas; et al., "Hallmarks of 'BRCAness' in sporadic cancers", Nature Reviews, Oct. 2004, 4:1-6.
Wooster, Richard; et al., "Breast and Ovarian Cancer", The New England Journal of Medicine, Jun. 5, 2003, 348:2339-47.
Bernstein, C., et al., "DNA repair/pro-apoptotic dual-role proteins in five major DNA repair pathways: fail-safe protection against carcinogenesis," (2002) *Mutation Research*, 511:145-178.
Bryant, H., et al., "Specific killing of BRCA2-deficient tumours with inhibitors of poly(ADP-ribose) polymerase," (2005) *Nature*, 434:913-917.

(Continued)

Primary Examiner — Brandon Fetterolf
Assistant Examiner — Anna Pagonakis
(74) Attorney, Agent, or Firm — Bozicevic, Field & Francis LLP; Pamela J. Sherwood

(57) ABSTRACT

The present invention relates to the recognition that inhibition of the base excision repair pathway is selectively lethal in cells which are deficient in HR dependent DNA DSB repair. Methods and means relating to the treatment of cancers which are deficient in HR dependent DNA DSB repair using inhibitors which target base excision repair components, such as PARP, is provided herein.

11 Claims, 18 Drawing Sheets

OTHER PUBLICATIONS

Elbashir, S., et al., "Duplexes of 21-nucleotide RNAs mediate RNA interference in cultured mammalian cells," (2001) *Nature*, 411:494-498.

Farmer, H., et al., "Targeting the DNA repair defect in *BRCA* mutant cells as a therapeutic strategy," (2005) *Nature*, 434:917-921.

Larminat, F., et al., "Deficiency in BRCA2 leads to increase in non-conservative homologous recombination," (2002) *Oncogene*, 121:5188-5192.

Massuda, E., et al., "GPI 6150, a PARP inhibitor, down-regulates metastasis associated S100A4 (Mts1) and suppresses invasion of breast cancer cells in vitro," (2003) *Proceedings of the American Association for Cancer Research*, 4($2^{nd}$ ed.):867-868.

Schultz, N., et al., "Poly(ADP-ribose) polymerase (PARP-1) has a controlling role in homologous recombination," (2003) *Nucleic Acids Research*, 31(17):4959-4964.

Shall, S., et al., "Ply(ADP-ribose) polymerase-1: what have we learned formt he deficient mouse model?" (2000) *Mutation Research*, 460:1-15.

Watchers, F., et al., "Selective targeting of homologous DNA recombination repair by gemcitabine," (2003) *Int. J. Radiation Oncology Biol. Phys.*, 57(2):553-562.

Weltin, D., et al, "Effect of 6(5H)-phenathridinone, as inhibitor of poly(ADP-ribose) polymerase, on cultured tumor cells," (1994) *Oncology Research*, 6(9):399-403.

Gallmeier et al., Absence of Specific Cell Killing of the BRCA2-Deficient Human Cancer Cell Line CAPAN1 by Poly(ADP-Ribose) Polymerase Inhibition, 2005 Cancer Biol. & Ther., 4(7): 703-706.

McCabe et al., BRCA2-Deficient CAPAN-1 Cells Are Extremely Sensitive to the Inhibition of Poly (ADP-Ribose) Polymerase, 2005, Cancer Biol. & Ther., 4(9): 934-936.

Banasik, Marek; et al., "Specific Inhibitors of Poly (ADP-Ribose) Synthetase and Mono (ADP-Ribosyl) transferase", The Journal of Biological Chemistry, Jan. 25, 1992, 267(3):1569-1575.

Calabrese, Christopher R; et al., "Identification of Potent Nontoxic Poly (ADP-Ribose) Polymerase-1 Inhibitors: Chemopotentiation and Pharmacological Studies", Clinical Cancer Research, Jul. 2003, 9:2711-2718.

Cepeda, Victoria; et al., "Poly (ADP-Ribose) Polymerase-1 (PARP-1) Inhibitors in Cancer Chemotherapy", Recent Patents on Anti-Cancer Drug Discovery, 2006, 1:39-53.

Dillon, Krystyna J; et al., "A FlashPlate Assay for the Identification of PARP-1 Inhibitors", J. Biomol Screen, 2003, 8(3):347-352.

Ferraris, Dana; et al., "Design and Synthesis of Poly ADP-ribose Polymerase-1 Inhibitors. 2. Biological Evaluation of Aza-5[H]-phenanthridin-6-ones as Potent, Aqueous-Soluble Compounds for the Treatment of Ischemic Injuries", J. Med. Chem., 2003, 46:3138-3151.

Griffin, RJ; et al., "The role of inhibitors of poly (ADP-ribose) polymerase as resistance-modifying agents in cancer therapy", Biochimie, 1995, 77:408-422.

McCabe, Nuala; et al., "Deficiency in the Repair of DNA Damage by Homologous Recombination and Sensitivity to Poly (ADP-Ribose) Polymerase Inhibition", Cancer Res, Aug. 15, 2006, 66(16):8109-8115.

Turner, Nicholas; et al., "Hallmarks of 'BRCAness' in sporadic cancers", Nature Reviews, Cancer, Oct. 2004, 4:1-6.

Virag, Laszlo; et al., "The Therapeutic Potential of Poly (ADP-Ribose) Polymerase Inhibitors", Pharmacological Reviews, 2002: 54(3):375-429.

BG483078, http://mgc.nci.nih.gov/, National Institutes of Health, Mammalian Gene Collection (MGC, Unpublished, 1999, Contact: Robert Strausberg, Ph.D, Tissue Procurement: CLONTECH Laboratories, Inc.

Dudas, Andrej; et al., "DNA double-strand break repair by homologous recombination", Mutation Research, 2004, 566:131-167.

Hoeijmakers, Jan H. J.; et al., "Genome maintenance mechanisms for preventing cancer", Nature, May 17, 2001, 411:366-374.

Khanna, Kum Kum; et al., "DNA double-strand breaks: signaling, repair and the cancer connection", Nature Genetics, Mar. 2001, 27:247-254.

Fong; et al., "AZD2281 (KU-0059436), a PARP (poly ADP-ribose polymerase) inhibitor with single agent anticancer activity in patients with BRCA deficient ovarian cancer: Results from a phase I study", J Clin Oncol 26: 2008 (May 20 suppl; abstr 5510).

Hao; et al., "BRCA1-IRIS activates cyclin D1 expression in breast cancer cells by downregulating the JNK phosphatase DUSP3/VHR", Int. J. Cancer (2007), 121:39-46.

Lau; et al., "Pre-clinical activity of the PARP inhibitor AZD2281 in homologous recombination repair deficient triple negative breast cancer", EORTIC 2008 Geneva, poster #557.

Bhattacharyya; et al., "The Breast Cancer Susceptibility Gene BRCA1 Is Required for Subnuclear Assembly of Rad51 and Survival following Treatment with the DNA Cross-linking Agent Cisplatin", The Journal of Biological Chemistry (2000), 725(31):23899-23903.

Canan Koch; et al., "Novel Tricyclic Poly(ADP-ribose) Polymerase-1 Inhibitors with Potent Anticancer Chemopotentiating Activity: Design, Synthesis, and X-ray Cocrystal Structure", J. Med. Chem. (2002), 45:4961-4974.

Digweed; et al., "Attenuation of the formation of DNA-repair foci containing RAD51 in Fanconi anaemia", Carcinogenesis (2002), 23(7):1121-1126.

Drew; et al., "PARP inhibitors in cancer therapy: Two modes of attack on the cancer cell widening the clinical applications", Drug Resistance Updates (2009), 12:153-156.

Fong; et al., "Inhibition of Poly(ADP-Ribose) Polymerase in Tumors from BRCA Mutation Carriers", The New England Journal of Medicine (2009), 361(2):123-134.

Gien; et al., "The Emerging Role of PARP Inhibitors in the Treatment of Epithelial Ovarian Cancer", Journal of Oncology (2010), ID: 151750, 6 pages.

Johnson; et al., "Relationships between drug activity in NCI preclinical in vitro and in vivo models and early clinical trials", British Journal of Cancer (2001), 84(10):1424-1431.

Liu, "XRCC2 Is Required for the Formation of Rad51 Foci Induced by Ionizing Radiation and DNA Cross-Linking Agent Mitomycin C", Journal of Biomedicine and Biotechnology (2002), 2(2):106-113.

Rodon; et al., "Development of PARP inhibitors in oncology", Expert Opinion Investig. Drugs (2009), 18(1):31-43.

Sausville; et al., Contributions of Human Tumor Xenografts to Anticancer Drug Development, Cancer Res. (2006), 66:335-3354.

Southan; et al., "Poly(ADP-Ribose) Polymerase Inhibitors", Current Medicinal Chemistry (2003), 10:321-340.

Tarsounas; et al., "BRCA2-dependent and independent formation of RAD51 nuclear foci", Oncogene (2003), 22:1115-1123.

Thacker, "The RAD51 gene family, genetic instability and cancer", Cancer Letters (2005), 219:125-135.

Menissier; et al., "Early Embryonic Lethality in PARP-1 Atm Double-Mutant Mice Suggest a Functional Synergy in Cell Proliferation during Development", Molecular and Cellular Biology (2001), 21(5):1828-1832.

Tentori; et al., "Potential Clinical Applications of Poly (ADP-RIBOSE) Polymerase (PARP) Inhibitors", Pharmacological Research (2002), 45(2):73-85.

* cited by examiner

KU-0058684

PARP-1 IC$_{50}$ = 3.2nM

KU-0058948

PARP-1 IC$_{50}$ = 3.4nM

KU-0051529

PARP-1 IC$_{50}$ = 3.4nM

DNA DAMAGE REPAIR INHIBITORS FOR THE TREATMENT OF CANCER

BACKGROUND OF THE INVENTION

This invention relates to the induction of cellular lethality in cancer cells, in particular cancer cells that are deficient in homologous recombination (HR) dependent DNA double strand break (DSB) repair.

The effective repair of DNA damage in cells relies on mechanisms of damage sensing followed by the transduction of damage signals to downstream effectors that arrest at cell cycle checkpoints and repair DNA damage. Cells contain a number of distinct pathways of signals and effectors that mediate the repair of different types of DNA damage. These pathways include base excision repair (BER), homologous recombination (HR) dependent DNA double strand break (DSB) repair, non-homologous end joining (NHEJ), nucleotide excision repair (NER), base excision repair (BER) and mismatch repair (MMR). The interaction and interdependence between the various DNA repair pathways remains poorly understood.

SUMMARY OF THE INVENTION

The present inventors have discovered that the inhibition of the BER pathway, for example by inhibition of poly(ADP-ribose)polymerase (PARP), is selectively lethal to those cancer cells that are deficient in HR dependent DNA DSB repair pathway. This has important implications in the treatment of cancer conditions.

One aspect of the invention provides the use of an inhibitor of a base excision repair pathway in the manufacture of a medicament for use in the treatment of cancer in an individual, wherein said cancer is deficient in HR dependent DNA DSB repair activity.

A method of treatment of cancer in an individual may comprise: administering an inhibitor of a base excision repair pathway to said individual, wherein said cancer is deficient in the HR dependent DNA DSB repair pathway.

The cancer may comprise one or more cancer cells having a reduced or abrogated ability to repair DNA by said second repair pathway relative to normal cells.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include ATM (NM_000051), RAD51 (NM_002875), RAD51L1 (NM_002877), RAD51C (NM_002876), RAD51L3 (NM_002878), DMC1 (NM_007068), XRCC2 (NM 005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485); where the designations refer to Genbank accession numbers. Other proteins involved in the HR dependent DNA DSB repair pathway include regulatory factors such as EMSY (Hughes-Davies et al, Cell, Vol 115, pp 523-535).

The base excision repair (BER) pathway repairs DNA single strand breaks and gaps and removes specific damaged bases. Gaps in the DNA helix are filled by the sequential action of a Poly(ADP-Ribose) Polymerase (PARP) and a ligase. (K. K. Khanna and S. P. Jackson, Nat. Genet., 27(3): 247-254 (2001); F. Dantzer et al. *Biochemistry* 39, 7559-69 2000; J. H. Hoeijmakers, *Nature* 411 366-74 (2001)). An inhibitor of base excision repair may inhibit any one of the components of the base excision repair pathway. Components of the BER pathway include: UNG (NM_003362), SMUG1 (NM_014311), MBD4 (NM_003925), TDG (NM_003211), OGG1 (NM_002542), MYH (NM_012222), NTHL1 (NM_002528), MPG (NM_002434), NEIL1 (NM_024608), NEIL2 (NM_145043), NEIL3 (NM_018248), APE1 (NM_001641), APE2 (NM_014481), LIG3 (NM_013975), XRCC1 (NM_006297), ADPRT (PARP1) (NM_0016718) and ADPRTL2 (PARP2) (NP_005475).

BER inhibitors may be used in the treatment of HR dependent DNA DSB repair deficient cancers in combination with a DNA damaging agent. Preferably, the DNA damaging agent is used in a dosage or formulation that, in the absence of the BER inhibitor, is not lethal to cells. Suitable DNA damaging chemotherapeutic agents are described below.

In some preferred embodiments, an inhibitor of the mammalian enzyme poly(ADP-ribose)polymerase (PARP) (D'Amours et al, (1999) Biochem. J. 342: 249-268) may be employed. A PARP inhibitor may thus be used for the treatment of a cancer which is deficient in HR dependent DNA DSB repair.

A method of treatment of a cancer deficient in HR dependent DNA DSB repair in an individual may comprise: administering a PARP inhibitor to said individual.

A PARP inhibitor may be used in the manufacture of a medicament for use in the treatment of cancer in an individual, wherein said cancer is deficient in HR dependent DNA DSB repair.

PARP inhibitors are described in more detail below.

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood et al (2001) Science 291 1284-1289) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2 i.e. expression and/or activity of BRCA1 and/or BRCA2 may be reduced or abolished in the cancer cells, for example by means of mutation or polymorphism in the encoding nucleic acid, or by means of mutation or polymorphism in a gene encoding a regulatory factor, for example the EMSY gene which encodes a BRCA2 regulatory factor (Hughes-Davies et al, Cell, Vol 115, pp 523-535).

BRCA1 and BRCA2 are known tumour suppressors whose wild-type alleles are frequently lost in tumours of heterozygous carriers (Jasin M. Oncogene. 2002 Dec. 16; 21(58): 8981-93; Tutt et al Trends Mol Med. (2002)8(12):571-6). The association of BRCA1 and/or BRCA2 mutations with breast cancer is well-characterised in the art (Radice P J Exp Clin Cancer Res. 2002 September; 21(3 Suppl):9-12). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some embodiments, a cancer condition in an individual may have been previously identified as a cancer which is deficient in HR dependent DNA DSB repair.

In other embodiments, a method as described herein may comprise the step of identifying a cancer condition in an individual as deficient in HR dependent DNA DSB repair.

A cancer may be identified as a HR dependent DNA DSB repair deficient cancer, for example, by determining the activity of the HR dependent DNA DSB repair pathway in one or more cancer cells from a sample obtained from the individual or by determining the activity of one or more components of the pathway. Activity may be determined relative to normal (i.e. non-cancer) cells, preferably from the same tissue.

The activity of the HR dependent DNA DSB repair pathway may be determined by measuring the formation of foci containing Rad51 in the nucleus in response to DNA damaging agents or PARP inhibitors. Cells deficient in the HR dependent DNA DSB repair pathway lack the ability to produce such foci. The presence of Rad51 foci may be determined using standard immunofluorescent techniques.

Other methods for determining the activity of the HR dependent DNA DSB repair pathway may include sensitivity to IR, chemotherapeutics such as inter-strand cross linking reagents, DSB inducing agents (Topoisomerase I & II inhibitors) as well as the use of western blot analysis, immunohistology, chromosomal abnormalities, enzymatic or DNA binding assays and plasmid-based assays.

In some embodiments, a cancer may be identified as deficient in an HR dependent DNA DSB repair pathway by determining the presence in cancer cells from the individual of one or more variations, for example, polymorphisms or mutations, in a nucleic acid encoding a polypeptide which is a component of the HR dependent DNA DSB repair pathway.

Sequence variations such as mutations and polymorphisms may include a deletion, insertion or substitution of one or more nucleotides, relative to the wild-type nucleotide sequence. In some embodiments, the variation may be a gene amplification, for example an amplification of the EMSY gene (CAD22881; gene symbol C11ORF30). The one or more variations may be in a coding or non-coding region of the nucleic acid sequence and, may reduce or abolish the expression or function of the HR dependent DNA DSB repair pathway component polypeptide. In other words, the variant nucleic acid may encode a variant polypeptide which has reduced or abolished activity or may encode a wild-type polypeptide which has little or no expression within the cell, for example through the altered activity of a regulatory element. A variant nucleic acid may have one, two, three, four or more mutations or polymorphisms relative to the wild-type sequence.

The presence of one or more variations in a nucleic acid which encodes a component of the HR dependent DNA DSB repair pathway, may be determined by detecting, in one or more cells of a test sample, the presence of an encoding nucleic acid sequence which comprises the one or more mutations or polymorphisms, or by detecting the presence of the variant component polypeptide which is encoded by the nucleic acid sequence.

Various methods are available for determining the presence or absence in a sample obtained from an individual of a particular nucleic acid sequence, for example a nucleic acid sequence which has a mutation or polymorphism that reduces or abrogates the expression or activity of a HR dependent DNA DSB repair pathway component. Furthermore, having sequenced nucleic acid of an individual or sample, the sequence information can be retained and subsequently searched without recourse to the original nucleic acid itself.

Thus, for example, scanning a database of sequence information using sequence analysis software may identify a sequence alteration or mutation.

Methods according to some aspects of the present invention may comprise determining the binding of an oligonucleotide probe to nucleic acid obtained from the sample, for example, genomic DNA, RNA or cDNA. The probe may comprise a nucleotide sequence which binds specifically to a nucleic acid sequence which contains one or more mutations or polymorphisms and does not bind specifically to the nucleic acid sequence which does not contain the one or more mutations or polymorphisms, or vice versa.

The oligonucleotide probe may comprise a label and binding of the probe may be determined by detecting the presence of the label.

A method may include hybridisation of one or more (e.g. two) oligonucleotide probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance, DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridization overnight at 42° C. in 6×SSC and washing in 6×SSC at a series of increasing temperatures from 42° C. to 65° C.

Other suitable conditions and protocols are described in Molecular Cloning: a Laboratory Manual: 3rd edition, Sambrook & Russell (2001) Cold Spring Harbor Laboratory Press NY and Current Protocols in Molecular Biology, Ausubel et al. eds. John Wiley & Sons (1992).

Nucleic acid, which may be genomic DNA, RNA or cDNA, or an amplified region thereof, may be sequenced to identify or determine the presence of polymorphism or mutation therein. A polymorphism or mutation may be identified by comparing the sequence obtained with the database sequence of the component, as set out above. In particular, the presence of one or more polymorphisms or mutations that cause abrogation or loss of function of the polypeptide component, and thus the HR dependent DNA DSB repair pathway as a whole, may be determined.

Sequencing may be performed using any one of a range of standard techniques. Sequencing of an amplified product may, for example, involve precipitation with isopropanol, resuspension and sequencing using a TaqFS+ Dye terminator sequencing kit. Extension products may be electrophoresed on an ABI 377 DNA sequencer and data analysed using Sequence Navigator software.

A specific amplification reaction such as PCR using one or more pairs of primers may conveniently be employed to amplify the region of interest within the nucleic acid sequence, for example, the portion of the sequence suspected of containing mutations or polymorphisms. The amplified nucleic acid may then be sequenced as above, and/or tested in any other way to determine the presence or absence of a mutation or polymorphism which reduces or abrogates the expression or activity of the HR dependent DNA DSB repair pathway component.

Suitable amplification reactions include the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)).

In some embodiments, a cancer may be identified as deficient in a HR dependent DNA DSB repair by assessing the level of expression or activity of a positive or negative regulator of a component of the HR dependent DNA DSB repair pathway, such as EMSY. Expression levels may be determined, for example, by Western blot, ELISA, RT-PCR, nucleic acid hybridisation or karyotypic analysis.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP699754, EP705903, Neuhausen S. L. and Ostrander E. A. Genet. Test (1992) 1, 75-83; Chappnis, P. O. and Foulkes, W. D. Cancer Treat Res (2002) 107, 29-59; Janatova M et al Neoplasma. 2003: 50(4):246-50; Jancarkova N Ceska Gynekol. 2003 68(1): 11-6). Determination of amplification of the BRCA2 binding factor EMSY is described in Hughes-Davies et al Cell 115 523-535).

Mutations and polymorphisms associated with cancer may also be detected at the protein level by detecting the presence of a variant (i.e. a mutant or allelic variant) polypeptide.

A method of identifying a cancer cell in a sample from an individual as deficient in HR dependent DNA DSB repair may include contacting a sample with a specific binding member directed against a variant (e.g. a mutant) polypeptide component of the pathway, and determining binding of the specific binding member to the sample. Binding of the specific binding member to the sample may be indicative of the presence of the variant polypeptide component of the HR dependent DNA DSB repair pathway in a cell within the sample.

Preferred specific binding molecules for use in aspects of the present invention include antibodies and fragments or derivatives thereof ('antibody molecules').

The reactivities of a binding member such as an antibody on normal and test samples may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding binding molecule (e.g. antibody) and reporter molecule.

The mode of determining binding is not a feature of the present invention and those skilled in the art are able to choose a suitable mode according to their preference and general knowledge.

Cancer cells in general are characterised by abnormal proliferation relative to normal cells and typically form clusters or tumours in an individual having a cancer condition.

A cancer condition which is deficient in the HR dependent DNA DSB repair pathway as described herein may include any type of solid cancer or malignant lymphoma and especially leukaemia, sarcomas, skin cancer, bladder cancer, breast cancer, uterus cancer, ovary cancer, prostate cancer, lung cancer, colorectal cancer, cervical cancer, liver cancer, head and neck cancer, oesophageal cancer, pancreas cancer, renal cancer, stomach cancer and cerebral cancer. In some preferred embodiments, the cancer condition may be breast, ovary, pancreas or prostate cancer. Cancers may be familial or sporadic.

A sample obtained from an individual may be a tissue sample comprising one or more cells, for example a biopsy from a cancerous tissue as described above, or a non-cancerous tissue, for example for use as a control.

Methods of the invention may be useful in assessing an individual having a cancer condition, for example in order to determine a therapeutic course of action. A method of assessing an individual having a cancer condition may comprise;

identifying a cancer cell obtained from the individual as deficient in HR dependent DNA DSB repair relative to normal cells, and;

providing a inhibitor of the BER pathway suitable for administration to said individual.

In some preferred embodiments, the BER pathway inhibitor is a PARP inhibitor. PARP inhibitors are described in more detail below. A method of assessing a cancer condition may comprise;

identifying a cancer cell obtained from the individual as deficient in HR dependent DNA DSB repair relative to normal cells, and;

providing a PARP inhibitor suitable for administration to said individual.

In some preferred embodiments, the cancer cell which is identified as deficient in HR dependent DNA DSB repair may have a BRCA1 or BRCA2 deficient phenotype.

An individual may have a predisposition to a cancer which is deficient in HR dependent DNA DSB repair. Methods and means of the invention are particularly useful for such individuals.

An individual may, for example, be heterozygous for a mutation or polymorphism in a nucleic acid encoding a component of the HR dependent DNA DSB repair pathway, for example a nucleic acid encoding a component described above.

A method of treatment of cancer in an individual may comprise;

administering a BER pathway inhibitor to said individual, wherein said individual is heterozygous for a mutation or polymorphism in a gene encoding a component of the HR dependent DNA DSB repair pathway.

A BER inhibitor may be used in the manufacture of a medicament for use in the treatment of a cancer in an individual who is heterozygous for a mutation in a gene of a HR dependent DNA DSB repair pathway and a base excision repair inhibitor may be used in the treatment of a cancer in an individual who is heterozygous for a mutation in a gene which encodes a component of the HR dependent DNA DSB repair pathway.

In some preferred embodiments, an individual who is heterozygous for a mutation or polymorphism in a gene which encodes a component of the HR dependent DNA DSB repair pathway may be heterozygous for a mutation or polymorphism in BRCA1 and/or BRCA2.

A BER inhibitor suitable for use in a method described herein may be any compound or entity, such as a small organic molecule, peptide or nucleic acid, which inhibits, reduces or abolishes the activity of one or more components of the BER pathway.

In some preferred embodiments, the BER inhibitor may reduce or abolish the activity of the enzyme poly(ADP-ribose)polymerase (PARP).

The term PARP as used herein refers to PARP1 (EC 2.4.2.30, Genbank No: M32721) and/or PARP2 (Ame et al J. Biol. Chem. (1999) 274 15504-15511; Genbank No: AJ236912) unless context dictates otherwise.

Examples of compounds which are known PARP inhibitors and which may be used in accordance with the invention include:

1. Nicotinamides, such as 5-methyl nicotinamide and O-(2-hydroxy-3-piperidino-propyl)-3-carboxylic acid amidoxime, and analogues and derivatives thereof.
2. Benzamides, including 3-substituted benzamides such as 3-aminobenzamide, 3-hydroxybenzamide, 3-nitrosobenzamide, 3-methoxybenzamide and 3-chloroprocainamide, and 4-aminobenzamide, 1,5-di[(3-carbamoylphenyl)aminocarbonyloxy]pentane, and analogues and derivatives thereof.
3. Isoquinolinones and Dihydroisoquinolinones, including 2H-isoquinolin-1-ones, 3H-quinazolin-4-ones, 5-substituted dihydroisoquinolinones such as 5-hydroxy dihydroisoquinolinone, 5-methyl dihydroisoquinolinone, and 5-hydroxy isoquinolinone, 5-amino isoquinolin-1-one, 5-dihydroxyisoquinolinone, 3,4 dihydroisoquinolin-1(2H)-ones such as 3,4 dihydro-5-methoxy-isoquinolin-1(2H)-one and 3,4 dihydro-5-methyl-1(2H)isoquinolinone, isoquinolin-1(2H)-ones, 4,5-dihydro-imidazo[4,5,1-ij]quinolin-6-ones, 1,6,-naphthyridine-5(6H)-ones, 1,8-naphthalimides such as 4-amino-1,8-naphthalimide, isoquinolinone, 3,4-dihydro-5-[4-1(1-piperidinyl) butoxy]-1(2H)-isoquinolinone, 2,3-dihydrobenzo[de]isoquinolin-1-one, 1-11b-dihydro-[2H]benzopyrano[4,3,2-de]isoquinolin-3-one, and tetracyclic lactams, including benzpyranoisoquinolinones such as benzopyrano[4,3,2-de]isoquinolinone, and analogues and derivatives thereof.
4. Benzimidazoles and indoles, including benzoxazole-4-carboxamides, benzimidazole-4-carboxamides, such as 2-substituted benzoxazole 4-carboxamides and 2-substituted benzimidazole 4-carboxamides such as 2-aryl benzimidazole 4-carboxamides and 2-cycloalkylbenzimidazole-4-carboxamides including 2-(4-hydroxyphenyl) benzimidazole 4-carboxamide, quinoxalinecarboxamides, imidazopyridinecarboxamides, 2-phenylindoles, 2-substituted benzoxazoles, such as 2-phenyl benzoxazole and 2-(3-methoxyphenyl) benzoxazole, 2-substituted benzimidazoles, such as 2-phenyl benzimidazole and 2-(3-methoxyphenyl) benzimidazole, 1,3,4,5 tetrahydro-azepino[5,4,3-cd]indol-6-one, azepinoindoles and azepinoindolones such as 1,5 dihydro-azepino[4,5,6-cd]indolin-6-one and dihydrodiazapinoindolinone, 3-substituted dihydrodiazapinoindolinones, such as 3-(4-trifluoromethylphenyl)-dihydrodiazapinoindolinone, tetrahydrodiazapinoindolinone and 5,6, -dihydroimidazo[4,5,1-j,k][1,4]benzodiazepin-7(4H)-one, 2-phenyl-5,6-dihydro-imidazo[4,5,1-jk][1,4]benzodiazepin-7(4H)-one and 2,3, dihydro-isoindol-1-one, and analogues and derivatives thereof
5. Phthalazin-1(2H)-ones and quinazolinones, such as 4-hydroxyquinazoline, phthalazinone, 5-methoxy-4-methyl-1(2) phthalazinones, 4-substituted phthalazinones, 4-(1-piperazinyl)-1(2H)-phthalazinone, tetracyclic benzopyrano[4,3,2-de]phthalazinones and tetracyclic indeno[1,2,3-de]phthalazinones and 2-substituted quinazolines, such as 8-hydroxy-2-methylquinazolin-4-(3H)one, tricyclic phthalazinones and 2-aminophthalhydrazide, and analogues and derivatives thereof.
6. Isoindolinones and analogues and derivatives thereof.
7. Phenanthridines and phenanthridinones, such as 5[H] phenanthridin-6-one, substituted 5[H]phenanthridin-6-ones, especially 2-, 3-substituted 5[H]phenanthridin-6-ones and sulfonamide/carbamide derivatives of 6(5H)phenanthridinones, thieno[2,3-c]isoquinolones such as 9-amino thieno[2,3-c]isoquinolone and 9-hydroxythieno[2,3-c]isoquinolone, 9-methoxythieno[2,3-c]isoquinolone, and N-(6-oxo-5,6-dihydrophenanthridin-2-yl]-2-(N,N-dimethylamino}acetamide, substituted 4,9-dihydrocyclopenta[lmn]phenanthridine-5-ones, and analogues and derivatives thereof.
8. Benzopyrones such as 1,2-benzopyrone, 6-nitrosobenzopyrone, 6-nitroso 1,2-benzopyrone, and 5-iodo-6-aminobenzopyrone, and analogues and derivatives thereof.
9. Unsaturated hydroximic acid derivatives such as O-(3-piperidino-2-hydroxy-1-propyl)nicotinic amidoxime, and analogues and derivatives thereof.
10. Pyridazines, including fused pyridazines and analogues and derivatives thereof.
11. Other compounds such as caffeine, theophylline, and thymidine, and analogues and derivatives thereof.

Additional PARP inhibitors are described for example in U.S. Pat. No. 6,635,642, U.S. Pat. No. 5,587,384, WO2003080581, WO2003070707, WO2003055865, WO2003057145, WO2003051879, U.S. Pat. No. 6,514,983, WO2003007959, U.S. Pat. No. 6,426,415, WO2003007959, WO2002094790, WO2002068407, U.S. Pat. No. 6,476,048, WO2001090077, WO2001085687, WO2001085686, WO2001079184, WO2001057038, WO2001023390, WO2001021615, WO2001016136, WO2001012199, WO9524379, Banasik et al. J. Biol. Chem., 267:3, 1569-75 (1992), Banasik et al. Molec. Cell. Biochem. 138:185-97 (1994)), Cosi (2002) Expert Opin. Ther. Patents 12 (7), and Southan & Szabo (2003) Curr Med Chem 10 321-340 and references therein.

One preferred class of suitable PARP inhibitors includes phthalazinones such as 1(2H)-phthalazinone and derivatives thereof, as described in WO02/36576. In particular, compounds of the formula:

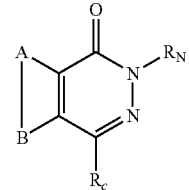

and isomers, salts, solvates, chemically protected forms, and prodrugs thereof, may be used for inhibiting PARP, wherein:
A and B together represent an optionally substituted, fused aromatic ring;
$R_C$ is represented by -L-$R_L$, where L is of formula:

$$-(CH_2)_{n1}-Q_{n2}-(CH_2)_{n3}-$$

wherein $n_1$, $n_2$ and $n_3$ are each selected from 0, 1, 2 and 3, the sum of $n_1$, $n_2$ and $n_3$ is 1, 2 or 3 and Q is selected from O, S, NH, C(=O) or —$CR_1R_2$—, where $R_1$ and $R_2$ are independently selected from hydrogen, halogen or optionally substituted $C_{1-7}$ alkyl, or may together with the carbon atom to which they are attached form a $C_{3-7}$ cyclic alkyl group, which may be saturated (a $C_{3-7}$ cycloalkyl group) or unsaturated (a $C_{3-7}$ cycloalkenyl group), or one of $R_1$ and $R_2$ may be attached to an atom in $R_L$ to form an unsaturated $C_{3-7}$ cycloalkenyl group which comprises the carbon atoms to which $R_1$ and $R_2$ are attached in Q, —$(CH_2)_{n3}$— (if present) and part of $R_L$; and $R_L$ is optionally substituted $C_{5-20}$ aryl; and
$R_N$ is selected from hydrogen, optionally substituted $C_{1-7}$ alkyl, $C_{3-20}$ heterocyclyl, and $C_{5-20}$ aryl, hydroxy, ether, nitro, amino, amido, thiol, thioether, sulfoxide and sulfone.

Preferably a compound of the formula:

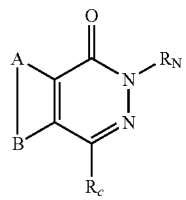

or an isomer, salt, solvate, chemically protected form, or prodrug thereof may be used to inhibit PARP,
wherein:
A and B together represent an optionally substituted, fused aromatic ring;
$R_C$ is —$CH_2$—$R_L$;
$R_L$ is optionally substituted phenyl; and
$R_N$ is hydrogen.

In some preferred embodiments, a compound having the structure of KU-0058684 or KU-0058948 as set out in FIG. 2, or an isomer, salt, solvate, chemically protected form, or prodrug thereof, may be used to inhibit PARP.

Suitable PARP inhibitors are either commercially available or may be synthesized by known methods from starting materials that are known (see, for example, Suto et al. Anticancer Drug Des. 6:107-17 (1991)).

Another class of base excision repair inhibitors includes peptide fragments of components of the BER pathway. For example, peptide fragments of the PARP sequence may be used to inhibit PARP and thus reduce or abolish activity of the BER pathway. Peptide fragments may be generated wholly or partly by chemical synthesis using the published sequences of the components, for example the published PARP sequence (Acc No: NM_001618). Peptide fragments can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Other candidate compounds for inhibiting a component of the BER pathway, such as PARP, may be based on modelling the 3-dimensional structure of the component and using rational drug design to provide candidate compounds with particular molecular shape, size and charge characteristics. A candidate inhibitor, for example, may be a "functional analogue" of a peptide fragment or other compound which inhibits the component. A functional analogue has the same functional activity as the peptide or other compound in question, i.e. it may interfere with the interactions or activity of the DNA repair pathway component. Examples of such analogues include chemical compounds which are modelled to resemble the three dimensional structure of the component in an area which contacts another component, and in particular the arrangement of the key amino acid residues as they appear.

Another class of suitable BER pathway inhibitors includes nucleic acid encoding part or all of the amino acid sequence of a component of the BER pathway, such as PARP (Acc No: NM_001618), or the complement thereof, which inhibit activity or function by down-regulating production of active polypeptide.

For example, the inhibition of PARP activity may be determined using conventional methods, including for example dot blots (Affar E B et al Anal Biochem. 1998; 259(2):280-3), and BER assays that measure the direct activity of PARP to form poly ADP-ribose chains for example by using radioactive assays with tritiated substrate NAD or specific antibodies to the polymer chains formed by PARP activity (K. J. Dillon et al, Journal of Biomolecular Screening, 8(3): 347-352 (2003).

For instance, expression of a BER pathway component may be inhibited using anti-sense or RNAi technology. The use of these approaches to down-regulate gene expression is now well-established in the art.

Anti-sense oligonucleotides may be designed to hybridise to the complementary sequence of nucleic acid, pre-mRNA or mature mRNA, interfering with the production of the base excision repair pathway component so that its expression is reduced or completely or substantially completely prevented. In addition to targeting coding sequence, anti-sense techniques may be used to target control sequences of a gene, e.g. in the 5' flanking sequence, whereby the anti-sense oligonucleotides can interfere with expression control sequences. The construction of anti-sense sequences and their use is described for example in Peyman and Ulman, Chemical Reviews, 90:543-584, (1990) and Crooke, Ann. Rev. Pharmacol. Toxicol. 32:329-376, (1992).

Oligonucleotides may be generated in vitro or ex vivo for administration or anti-sense RNA may be generated in vivo within cells in which down-regulation is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

The complete sequence corresponding to the coding sequence in reverse orientation need not be used. For example fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14-23 nucleotides, e.g. about 15, 16 or 17.

An alternative to anti-sense is to use a copy of all or part of the target gene inserted in sense, that is the same, orientation as the target gene, to achieve reduction in expression of the target gene by co-suppression; Angell & Baulcombe (1997) The EMBO Journal 16, 12:3675-3684; and Voinnet & Baulcombe (1997) Nature 389: pg 553). Double stranded RNA (dsRNA) has been found to be even more effective in gene silencing than both sense or antisense strands alone (Fire A. et al Nature 391, (1998)). dsRNA mediated silencing is gene specific and is often termed RNA interference (RNAi).

RNA interference is a two-step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

RNAi may also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologous genes in a wide range of mammalian cell lines (Elbashir S M. et al. Nature, 411, 494-498, (2001)).

Another possibility is that nucleic acid is used which on transcription produces a ribozyme, able to cut nucleic acid at a specific site—thus also useful in influencing gene expression. Background references for ribozymes include Kashani-Sabet and Scanlon, 1995, *Cancer Gene Therapy,* 2(3): 213-223, and Mercola and Cohen, 1995, *Cancer Gene Therapy,* 2(1), 47-59.

Methods of the invention may comprise administering a BER inhibitor, such as a PARP inhibitor, to an individual. This may occur subsequent to having identified the individual as having a cancer condition deficient in HR dependent DNA DSB repair.

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Pharmaceutical compositions comprising Base excision repair inhibitors as defined above, for example an inhibitor admixed together with one or more pharmaceutically acceptable carriers, excipients, buffers, adjuvants, stabilisers, or other materials, as described herein, may be used in the methods described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing the active compound into association with a carrier which may constitute one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

The BER inhibitor or pharmaceutical composition comprising the inhibitor may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer=s Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Compositions comprising BER pathway inhibitors may be used in the methods described herein in combination with standard chemotherapeutic regimes that damage cancer cell DNA. Suitable agents may include inhibitors of topoisomerase I and II activity, such as camptothecin, drugs such as irinotecan, topotecan and rubitecan, alkylating agents such as temozolomide and DTIC (dacarbazine), and platinum agents like cisplatin, cisplatin-doxorubicin-cyclophosphamide, carboplatin, and carboplatin-paclitaxel.

Other suitable chemotherapeutic agents include doxorubicin-cyclophosphamide, capecitabine, cyclophosphamide-methotrexate-5-fluorouracil, docetaxel, 5-fluoracil-epirubicin-cyclophosphamide, paclitaxel, vinorelbine, etoposide, pegylated liposomal doxorubicin and topotecan.

The treatment of individuals using such agents is well-known in the art.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

Methods of the invention may also be useful in investigating and assessing a cancer condition in an individual.

A method of assessing the activity of the HR dependent DNA DSB repair pathway in a cancer condition may comprise;

contacting a base excision repair inhibitor with a sample of cancer cells obtained from the individual having the condition, and;

determining the amount of cell death in said sample relative to a control sample.

An increase in cell death in the sample relative to control cells which have normal levels of HR dependent DNA DSB repair activity is indicative that the cancer is deficient in HR dependent DNA DSB repair.

The individual may have a cancer condition and the sample may be a sample of cancer cells, for example from a tumour biopsy.

In preferred embodiments, the base excision repair inhibitor is a PARP inhibitor. A method of assessing HR dependent DNA DSB repair in a cancer condition may thus comprise;

contacting a PARP inhibitor with a sample of cancer cells obtained from the individual having the cancer condition, and;

determining the amount of cell death in said sample relative to a control sample.

An increased sensitivity the PARP inhibitor in cells from the sample relative to control cells is indicative that the cancer is deficient in the HR dependent DNA DSB repair activity.

Increased sensitivity to PARP inhibitors may be indicative that the cancer cells have a BRCA1 or BRCA2 deficient phenotype, for example a reduction or abolition of BRCA1 or BRCA2 expression or activity.

A cancer condition identified as being deficient in HR dependent DNA DSB repair activity, for example a condition having a BRCA1 or BRCA2 deficient phenotype, may be subjected to therapies that are specifically directed at such conditions. Suitable therapies may include the use of DNA cross-linking agents such as Mitomycin C, cisplatin or carboplatin.

Methods may be used to predict the response of a cancer condition in an individual to a treatment targeting HR, for example a treatment specific to cancers having a BRCA1 or BRCA2 deficient phenotype.

A method of predicting the response of a cancer condition in an individual to a treatment targeting cancers deficient in HR dependent DNA DSB repair may comprise;

contacting a BER inhibitor, for example a PARP inhibitor, with a sample of cancer cells obtained from the individual having the cancer condition, and;

determining the amount of cell death in said sample relative to a control sample.

An increase in cell death in the sample relative to control cells which have normal levels of HR dependent DNA DSB repair activity (i.e. an increased sensitivity to PARP inhibitors) is indicative that the cancer may be responsive to said treatment.

Treatments which target cancers deficient in HR dependent DNA DSB repair, for example BRCA1 or BRCA2 deficient cancers, may include, for example, DNA cross-linking agents such as mitomycin C, cisplatin or carboplatin.

Other aspects of the invention relate to the use of an inhibitor of HR dependent DNA DSB repair in the treatment of a cancer that is deficient in base excision repair.

A method of treatment of a cancer deficient in base excision repair in an individual may comprise;

administering an HR dependent DNA DSB repair pathway inhibitor to said individual.

An HR dependent DNA DSB repair inhibitor may be used in the manufacture of a medicament for use in the treatment of cancer in an individual, wherein said cancer is deficient in base excision repair.

An inhibitor of HR dependent DNA DSB repair may include an inhibitor of one or more of the pathway components set out above. Suitable inhibitors include ATM inhibitors.

An ATM inhibitor may, for example, be a compound of formula I:

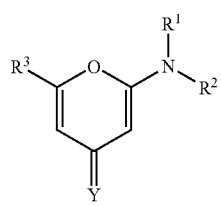

(I)

or an isomer, salt, solvate, chemically protected form, or prodrug thereof, wherein:
Y is either O or S;
$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; and
$R^3$ is a phenyl group attached to an optionally substituted $C_{5-20}$ carboaryl group by an ether or thioether bridge, the phenyl group and optionally substituted $C_{5-20}$ carboaryl group being optionally linked by a further bridge group, which is bound adjacent the ether or thioether bridge on both groups so as to form an optionally substituted $C_{5-7}$ oxygen or sulphur containing heterocycle fused to both the phenyl group and the $C_{5-20}$ carboaryl group, the phenyl group being further optionally substituted.

Such inhibitors are described in more detail in WO03/070726.

Other inhibitors include peptidyl fragments of components of HR dependent DNA DSB repair and encoding nucleic acids as described above.

A cancer condition may be identified as deficient in BER activity using a method described above.

Aspects of the present invention will now be illustrated with reference to the accompanying figures described below and experimental exemplification, by way of example and not limitation. Further aspects and embodiments will be apparent to those of ordinary skill in the art.

Various parameters and features of the invention are set out above. For the avoidance of doubt, it is stated that all combinations and sub-combinations of these parameters and features are encompassed by the present invention.

All documents mentioned in this specification are hereby incorporated herein by reference.

BRIEF DESCRIPTION OF THE DRAWINGS

FIG. 3 shows Brca1 wild type (11CO:|) heterozygous (Cre6:▲) and deficient (Cre10:●) ES cells under continuous exposure to PARP inhibitors (KU0058684, top; KU0058948, middle; KU0051529, bottom) Error bars represent standard errors of the mean.

FIG. 4 shows Brca2 wild type (D3:|), heterozygous (Cre6:▲) and deficient (Cre24:●) ES cells under continuous exposure to PARP inhibitors (KU0058684, top; KU0058948, middle; KU0051529, bottom). Error bars represent standard errors of the mean.

FIG. 5 shows Brca1 wild type (11CO:■), heterozygous (Cre6:▲) and deficient (Cre10:●) ES cells after 1 (left), 4 (middle) and 24 hour (right) timed exposures to KU0058684. Error bars represent standard errors of the mean.

FIG. 6 shows Brca2 wild type (D3:■), heterozygous (Cre6:▲) and deficient (Cre24:●) ES cells after 1 (left), 4 (middle) and 24 hour (right) timed exposures to KU0058684. Error bars represent standard errors of the mean.

FIG. 7 shows Brca1 wild type (11CO:top) and mutant (Cre10:bottom) cells treated with KU0058684 for 24 h at 0 nM (left), 10 nM (middle) or 1 µM (right) and analysed by FACS.

FIG. 8 shows Brca2 wild type (D3) and mutant (Cre24) cells treated with KU0058684 for 24 h at 0 nM (left), 10 nM (middle) or 1 µM (right) and analysed by FACS.

FIG. 12 shows phospho-histone H3 FACS data for Brca1 wild type (11CO:top) and mutant (Cre10:) ES cells and Brca2 wild type (D3) and mutant (Cre24) cells treated with KU0058684 for 24 h at 0 nM (left), 10 nM (middle) or 1 µM (right) and analysed by FACS.

FIG. 13 shows phospho-histone H3 FACS for VC8 and VC8BAC cells treated with 0 µM, 100 µM, 1 nM and 10 nM (left to right, respectively) KU0058684 for 24 h.

FIG. 14 shows clonogenic survival curves of Brca2 deficient (V-C8:|) and complemented (V-C8 BAC+:▲) cells under continuous exposure to PARP inhibitors (KU0058684: top, KU0058948: middle and KU0051529: bottom).

FIG. 15 shows clonogenic survival curves of Brca2 deficient (V-C8:|) and complemented (V-C8 BAC+:▲) cells after 1 hour (top), 4 hour (middle) and 24 hour (bottom) timed exposures to KU0058684. Error bars represent standard errors of the mean.

EXAMPLES

Materials and Methods

RNA Interference

Figure 1:
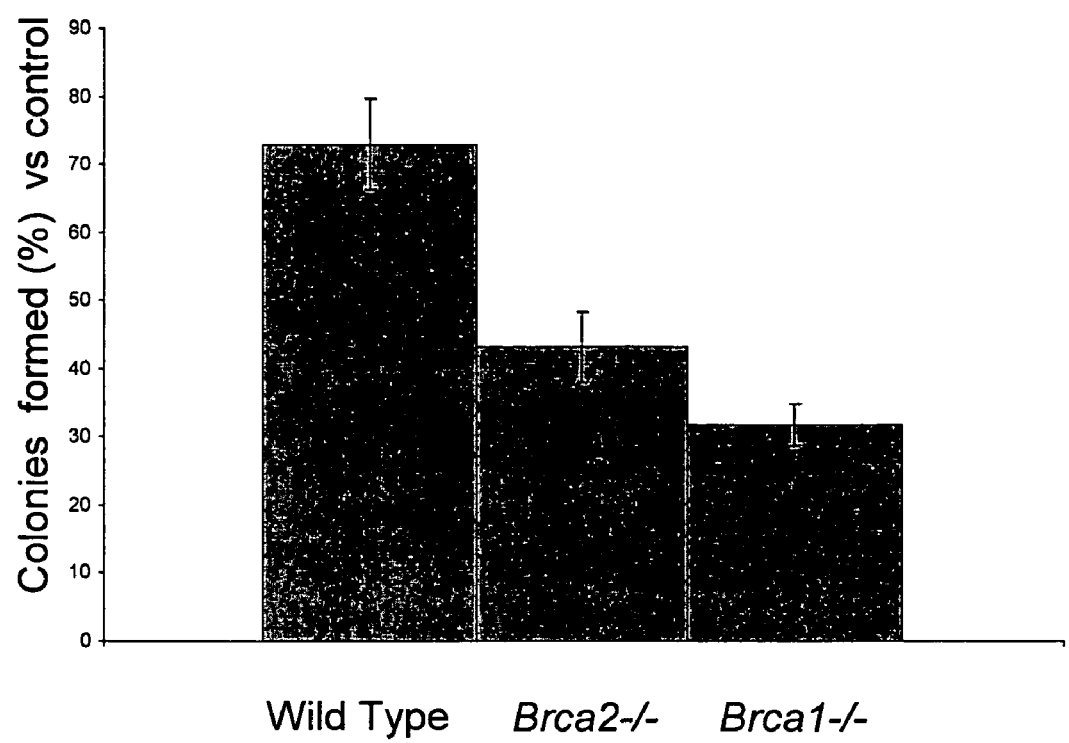
FIG. 1 shows that a reduction in the level of Parp1 reduces the viability of BRCA1 and BRCA2 mutant cells relative to wild-type cells.

Gene-specific pSUPER (T. R. Brummelkamp et al *Science* 296, 550-3 (2002)) constructs were generated expressing the following RNAi target sequences: (i) mouse Parp1 5'-GCG-GAGUACGCCAAGUCCA-3' (SEQ ID NO:1) (ii) scrambled control 5'-CAUGCCUGAUCCGCUAGUC-3' (SEQ ID NO:2).

A 1.6 kb fragment containing the CMV IE promoter and eCFP (enhanced cyan fluorescent protein) was subcloned from pECFP-Mito (Invitrogen) into the SapI site of the resultant pSUPER constructs, generating pSUPER-eCFP-Parp1 and pSUPER-eCFP-control. D3 ES cells were transfected with these plasmids using Lipofectamine 2000 (Invitrogen) according to the manufacturers instructions. Forty-eight hours after transfection, total cell lysates were generated using a buffer composed of 20 mM Tris pH 8, 200 mM NaCl, 1 mM EDTA, 0.5% (v/v) NP40, 10% (v/v) glycerol and protease inhibitors. 30 µg of each lysate was electrophoresed on Bis-Tris Acetate Acrylamide Pre Cast Gels (Novex) and blotted onto Trans-Blot Nitrocellulose (Biorad). Blots were probed with either Rabbit polyclonal anti-PARP-1 antibody (Cell Signalling, Cat No. 9542) or Rabbit anti-GFP/CFP antiserum (Invitrogen, Cat. No. R970-01), followed by a secondary hybridization with anti-rabbit IgG-HRP with subsequent chemiluminescent detection using ECL™ (Amersham, UK).

Small Molecule Inhibitors of PARP:

PARP inhibitors were synthesized as described in WO02/36576. Chemical inhibitors were dissolved in DMSO at 10 mM and stored at −20° C. in the dark.

Cell Lines

VC8 cells and the mouse Brca2 BAC complemented derivatives were as described in M. Kraakman-van der Zwet et al., *Mol Cell Biol* 22, 669-79 (2002)). ES cells defective in Brca2 function have been described previously (Tutt et al. (2002) *EMBO Rep* 3, 255-60). The construction of ES cells defective in Brca1 will be described elsewhere but have previously been validated (Foray et al. (2003) *Embo J* 22 2860-71). HBL100 cells were transfected with a pSUPER BRCA1 RNAi plasmid and selected with geneticin for 3 weeks. Clones were selected on the basis of their BRCA1 expression, as analysed by Northern blot.

Clonogenic Assays

For measurement of sensitivity to Parp1 RNA knockdown, ES cells maintained on tissue culture dishes coated with 0.1% gelatin were transfected as above, with either pSUPER-eCFP-Parp1 or pSUPER-eCFP-control along with a vector expressing resistance to the antibiotic, blasticidin (pEF-Bsd, Invitrogen). Twenty-four hours after transfection, cells were trypsinised and seeded in 6-well plates. Forty-eight hours post-transfection, treatment with blasticidin was commenced and cells were re-fed every three days. After 10-14 days, cells were washed with PBS, fixed in methanol and stained with crystal violet. Colonies containing greater than approximately 50 cells were counted.

For measurement of sensitivity to chemical inhibitors, cell cultures in exponential growth were trypsinised and seeded at various densities in 6-well plates onto Mitomycin C inactivated mouse embryonic fibroblasts and where appropriate treated with inhibitors after 18 h. For continuous exposure, cells were re-fed every 4 days with fresh medium and inhibitor. For timed exposures, inhibitor was added for the specified period then cells were washed and re-fed with fresh medium. After 10-14 days, cells were washed with PBS, fixed in methanol and stained with crystal violet. Colonies containing greater than approximately 50 cells were counted. Experiments were performed at least three times in triplicate.

FACS Analysis

For DNA content measurement, cells were fixed in 70% ethanol, incubated with Rnase A and propidium iodide (PI) and analysed with a FACSCalibur (Becton Dickinson). For phospho-Histone H3 analysis, cells were fixed in 70% ethanol, permeabilised with 0.25% triton X-100, incubated with anti-phospho-histone H3 antibody (Upstate Biotechnology) for 3 hours, and then with FITC-anti rabbit IgG (Serotec) for 30 minutes. Processing for FACS analysis was as above.

Apoptotic Analysis

Cells were trypsinised, retaining both culture supernatant and wash medium. These were pooled and the cells washed in cold PBS-A before resuspension at $1 \times 10^6$ cells/ml in binding buffer (10 mM HEPES, 140 mM NaCl, 2.5 mM $CaCl_2$ (pH7.4)). 100 µl suspension was incubated in the dark with 5 µl Annexin V-FITC (BD Biosciences)/0.1 µg propidium iodide for 15 mins at room temperature, 400 µl binding buffer added and analysed immediately on a FACS Calibur (BD Biosciences).

Rad 51 Focus Formation

ES cells were cultured for 48 h in various concentrations of PARP inhibitor fixed in 4% paraformaldehyde in PBS and permeabilised with 0.2% Triton X100 in PBS. Cells were stained with a 1:100 dilution of rabbit anti-Rad51 polyclonal antibody (Ab 551922, BD-Pharmingen, Oxford, UK). After washing, the primary antibody was visualised with Alexa Fluor-555 goat anti-rabbit IgG (Alexa) and nuclei with TO-PRO-3 iodide (Molecular Probes). Rad51 foci were visualised with and quantified using a Leica TCS-SP2 confocal microscope.

Comet Assay

VC8 and VC8-BAC cells were plated 24 hours prior to treatment with 1 µM KU0058684 for 30 hours. All further work was carried out in the dark. Cells were washed with and scraped into PBS prior to Comet analysis as described (Lemay and Wood, 1999). Cells suspended in LMP agarose (0.5% in PBS) were spread onto Comet slides (Trevigen, Gaithersburg) and placed at 4 C until set, prior to lysis for 45 mins in 2.5M NaCl, 100 mM EDTA, 10 mM Tris Base, 1% sodium lauryl sarcosinate, 0.01% Triton X-100. Slides were transferred to TBE for 5 mins prior to electrophoresis at 18V for 15 mins. Slides were then fixed in 100% ethanol for 5 mins and air dried before the addition of SYBR green dye and visualisation by epifluorescence using fluorescein filters (Nikon). Comets were analysed using the Comet software module of the Lucia G imaging package as supplied by Nikon. 50 comets per data point were examined for each of three independent experiments and the mean tail moment calculated.

Mitotic Chromosome Analysis

ES cells were seeded onto gelatin, treated for 24 hours with chemical inhibitors, followed by colcemid treatment for 1 hour. Cells were harvested, fixed, dropped onto slides, dried and stained with DAPI before chromosome analysis under a microscope.

ES Cell Xenografts and Treatment with KU0058684

Figure 16:
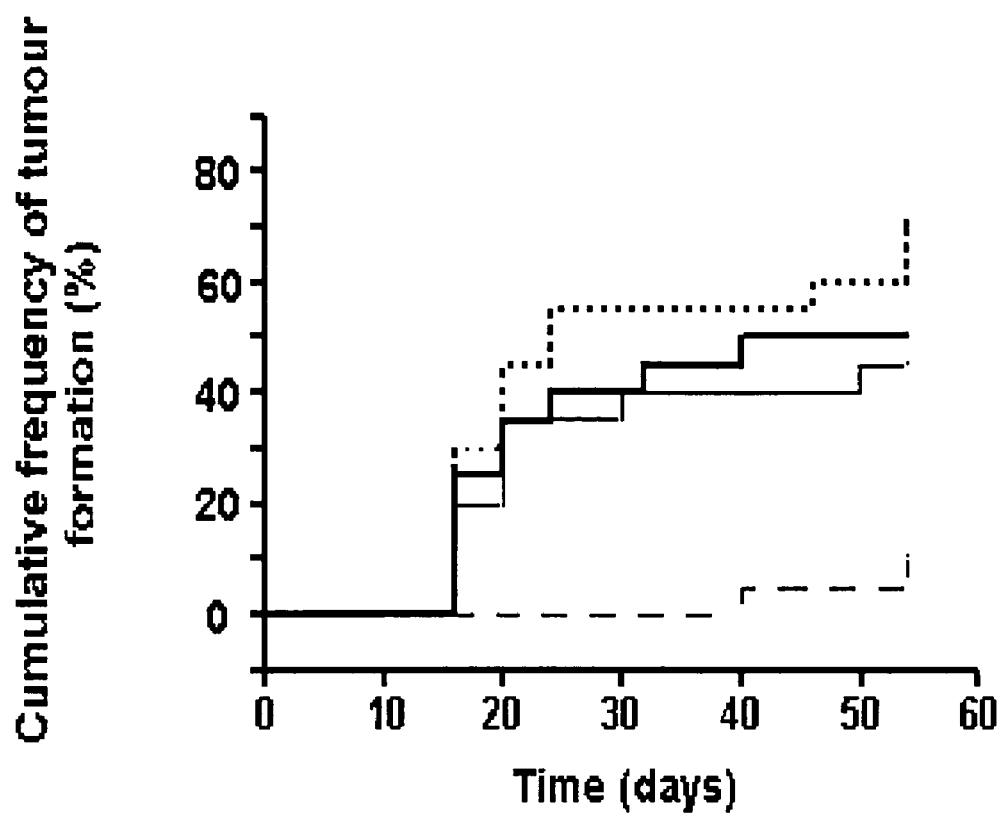
FIG. 16 shows tumour formation in ES xenografts and the effect of treatment with KU0058684; dotted line—wild type with vehicle, bold solid line—wild type with drug KU0058684, solid line—Brca2 deficient with vehicle, dashed line—Brca2 deficient with KU0058684.

ES cell derived tumours (teratomas) were produced by subcutaneous injection of $2\times10^8$ ES cells into 6-8 week athymic BALB/c nude (nu/nu) mice. Twenty mice were injected with Brca2 deficient ES cells and an identical cohort with isogenic wild type cells. Two days after cell injection, treatment with KU0058684 or vehicle was initiated. For three consecutive days, two intraperitoneal doses of KU0058684 (or vehicle) were administered, six hour apart, each at a dosage of 15 mg/kg animal. This treatment was then stopped for five days and then reinitiated (as before) for another three consecutive days. Growth of tumours was monitored from a minimum volume of 0.3 cm$^3$. The data in FIG. 16 represents two separate experiments involving in total 40 animals.

Production of BRCA1 Cell-Deficient Line

The MCF7 scrambled and MCF7-3.23 cell lines were generated by stable transfection of MCF7 mammary adenocarcinoma cells with gene specific pSUPER constructs. Gene specific pSUPER constructs were generated expressing the following RNAi target sequences: (i) human BRCA1 5'-GGAACCTGTCTCCACAAAG-3' (SEQ ID NO:3) (ii) scrambled control 5'-CATGCCTGATCCGCTAGTC-3' (SEQ ID NO:4). A 1.8 kb fragment containing the human EF1a promoter and the blasticidin resistance gene (bsd) was subcloned from pEFBsd (Invitrogen) into the SapI site of the resultant pSUPER constructs, generated pSUPER-Bsd-BRCA1 and pSUPER-Bsd-scrambled. MCF7 cells were transfected with these plasmids using FuGene6 (Roche) according to the manufacturers instructions. After selection in blasticidin, resistant clones were assessed by real time PCR for silencing of BRCA1 mRNA (Egawa et al Oncology. 2001; 61(4): 293-8; Egawa et al Int J Cancer. 2001 Jul. 20; 95(4): 255-9). Clones with reduced levels of BRCA1 mRNA were cultured (under blasticidin selection) over 8 passages and the real-time assay repeated. Cell line MCF7-3.23 was shown to have only 30% expression of BRCA1 compared to MCF7 clones possessing the construct pSUPER-Bsd-scrambled.

Results

Reduction of Parp1 Protein Levels by siRNA

A plasmid (pSUPER-eCFP-Parp1) expressing a Parp1 specific siRNA under the control of the H1 promoter (T. R. Brummelkamp et al, Science 296, 550-3 (2002)) and Enhanced Cyan Fluorescent Protein (eCFP) under the control of the CMV IE promoter was transfected into D3 mouse embryonic stem cells. As a control, a plasmid expressing an unrelated scrambled siRNA, pSUPER-eCFP-control was separately transfected. Forty-eight hours after transfection, cell lysates were prepared and analysed by western blotting. Blots were probed with either a polyclonal anti-PARP-1 antibody or an anti-GFP/CFP antiserum.

Levels of PARP1 in the Parp1 specific siRNA expressing cells were observed to be much lower than PARP1 levels in the control cells. Levels of eCFP were similar in both Parp1 siRNA expressing and control cells.

Reduction in the Viability of BRCA1 and BRCA2 Deficient Cells after Parp1-Specific siRNA Knockdown.

Wild type, Brca1$^{-/-}$ and Brca2$^{-/-}$ mouse embryonic stem (ES) cells were transfected with either pSUPER-eCFP-Parp1 or pSUPER-eCFP-control together with a blasticidin resistance-encoding plasmid pEF-Bsd in a 10:1 ratio. Blasticidin resistance clones were selected and quantitated. The results are shown in FIG. 1 plotted as the number of colonies after transfection of pSUPER-eCFP-Parp1 relative to the number after transfection of pSUPER-eCFP-control. Error bars are equal to one standard deviation around the mean.

After correction for transfection efficiency using the control siRNA, it was apparent that the survival of both Brca1 and Brca2 deficient ES cells was considerably reduced when the expression of Parp1 was inhibited.

Figure 2:
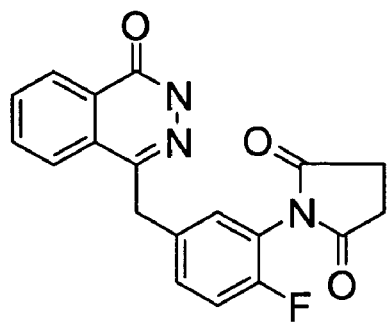
FIG. 2 shows the PARP inhibitors KU0058684, KU0058948 and KU0051529 and their $IC_{50}$s against PARP-1 enzyme activity.
Figure 2:
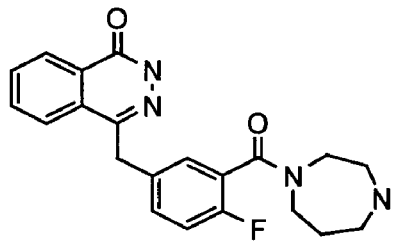
Figure 2:
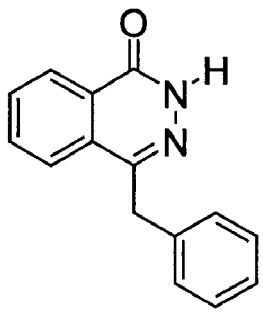

Reduction in the Viability of BRCA1 and BRCA2 Deficient Cells After Chemical PARP Inhibitors Chemical inhibitors of Parp activity were employed to confirm the selective inhibition of Brca1 and Brca2 deficient cells observed above. Two different PARP inhibitors, KU0058684, KU0058948 and a weakly active but chemically related compound KU0051529 were used (FIG. 2). These novel PARP inhibitors are based around a phthalazin-1-one core and are competitive inhibitors with respect to the PARP substrate NAD$^+$. KU0058684 and KU0058948 are potent and specific inhibitors of the poly(ADP-ribose) polymerase activity of the proteins PARP-1 and PARP-2 and do not inhibit vault PARP, tankyrase or PARP-3 at concentrations up to 1 µM. Conversely, KU0051529 is ~250× less effective in the inhibition of these enzymes despite being chemically related.

Figure 3:
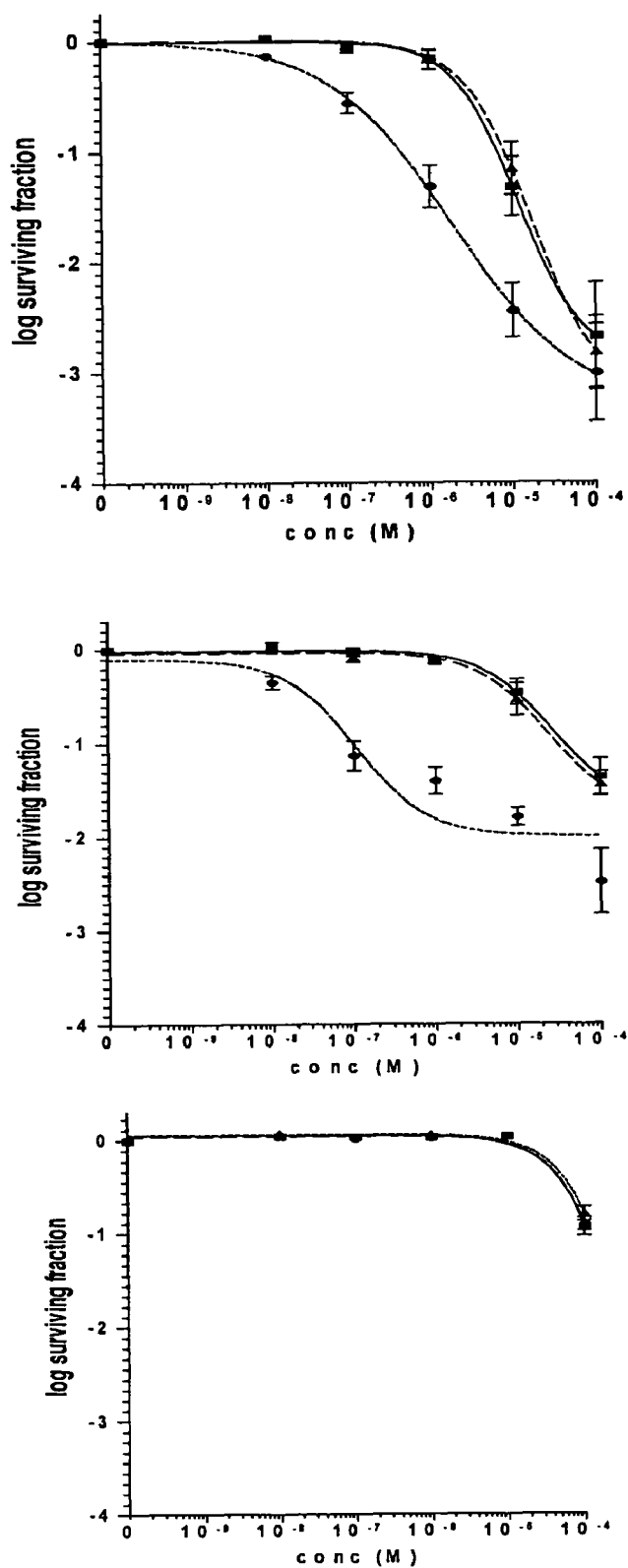
FIGS. 3 and 4 show clonogenic survival curves of cells exposed to PARP inhibitors.
Figure 4:
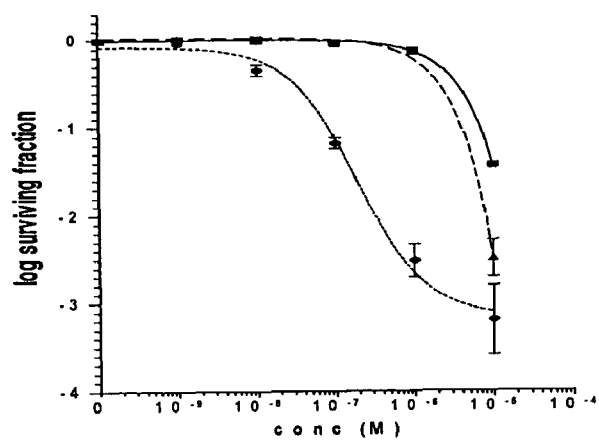
Figure 4:
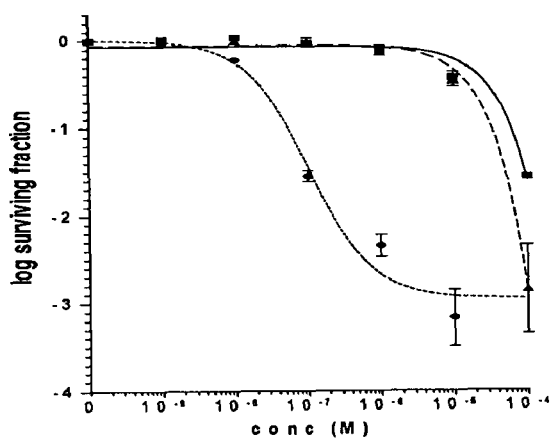
Figure 4:
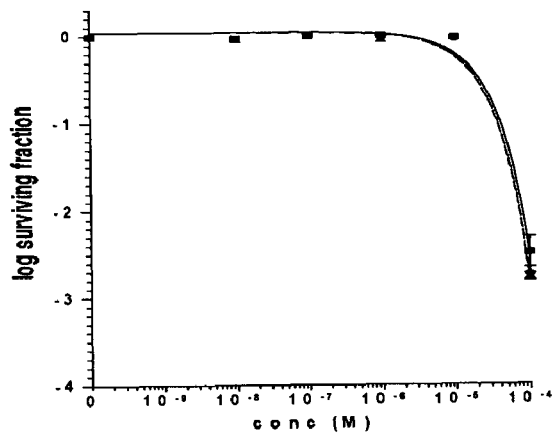
Figure 14:
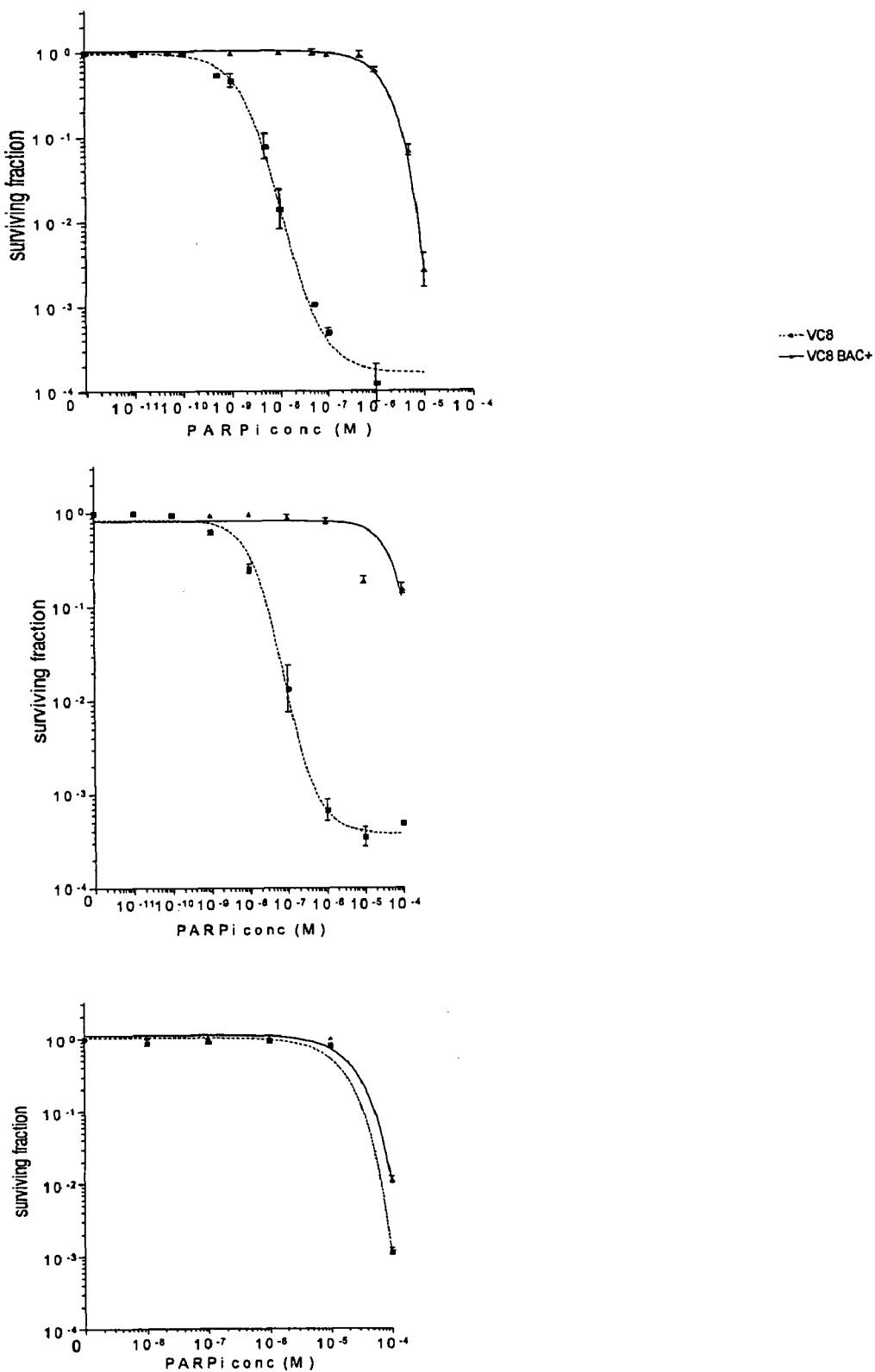
FIGS. 14 and 15 show an analysis of the effects of PARP inhibition in other cells lacking BRCA1 and BRCA2 function.
Figure 15:
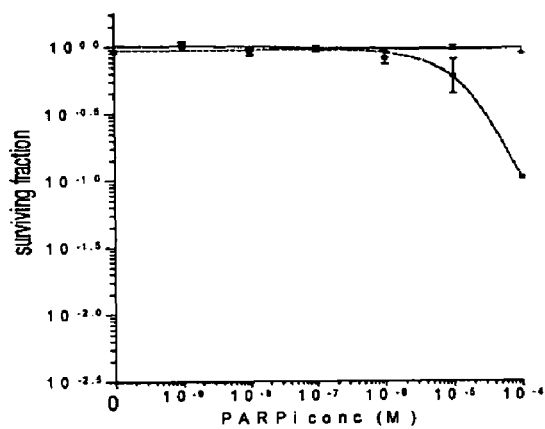
Figure 15:
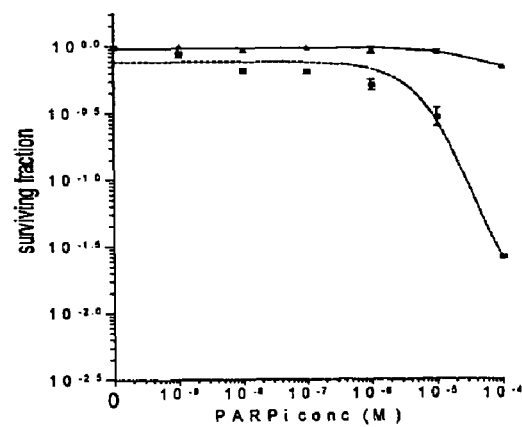
Figure 15:
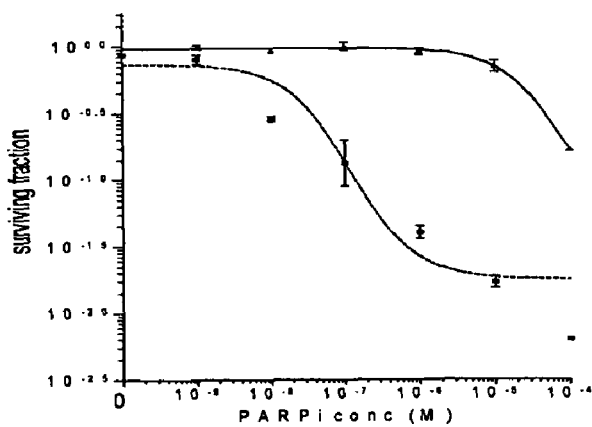

KU0058684, KU0058948 and KU0051529 were used to probe the sensitivity of cells deficient in Brca1 or Brca2 to the inhibition of PARP activity. Clonogenic assays showed that both Brca1 and Brca2 deficient cell lines were extremely sensitive to KU0058684 and KU0058948 compared to otherwise isogenic cells (FIG. 3, 4). The SF50 (dosage at which 50% of cells survived) for KU0058684 was $3.5\times10^{-8}$M for Brca1 and $1.5\times10^{-8}$M for Brca2; for wild-type cells this was around $3.5\times10^{-8}$M. This represents factors of 57-fold and 133-fold enhanced sensitivity for Brca1 and Brca2 mutant cells respectively compared to wild-type. Similar results were obtained with chinese hamster ovary cells deficient in Brca2, which showed a greater than 1000-fold enhanced sensitivity compared to a Brca2-complemented derivative (FIGS. 14 and 15). The sensitivity of Brca1 and Brca2 mutant cells to KU0058948 was even greater than that of KU0058684. In contrast, KU0051529 had no selective effect on cells lacking wild-type Brca1 or Brca2 compared to wild-type cells. This, in conjunction with the siRNA data, demonstrates that the mechanism of sensitivity is specifically through inhibition of PARP. Notably none of the inhibitors had any selective effect on cells heterozygous for Brca1 or Brca2 mutation.

Figure 5:
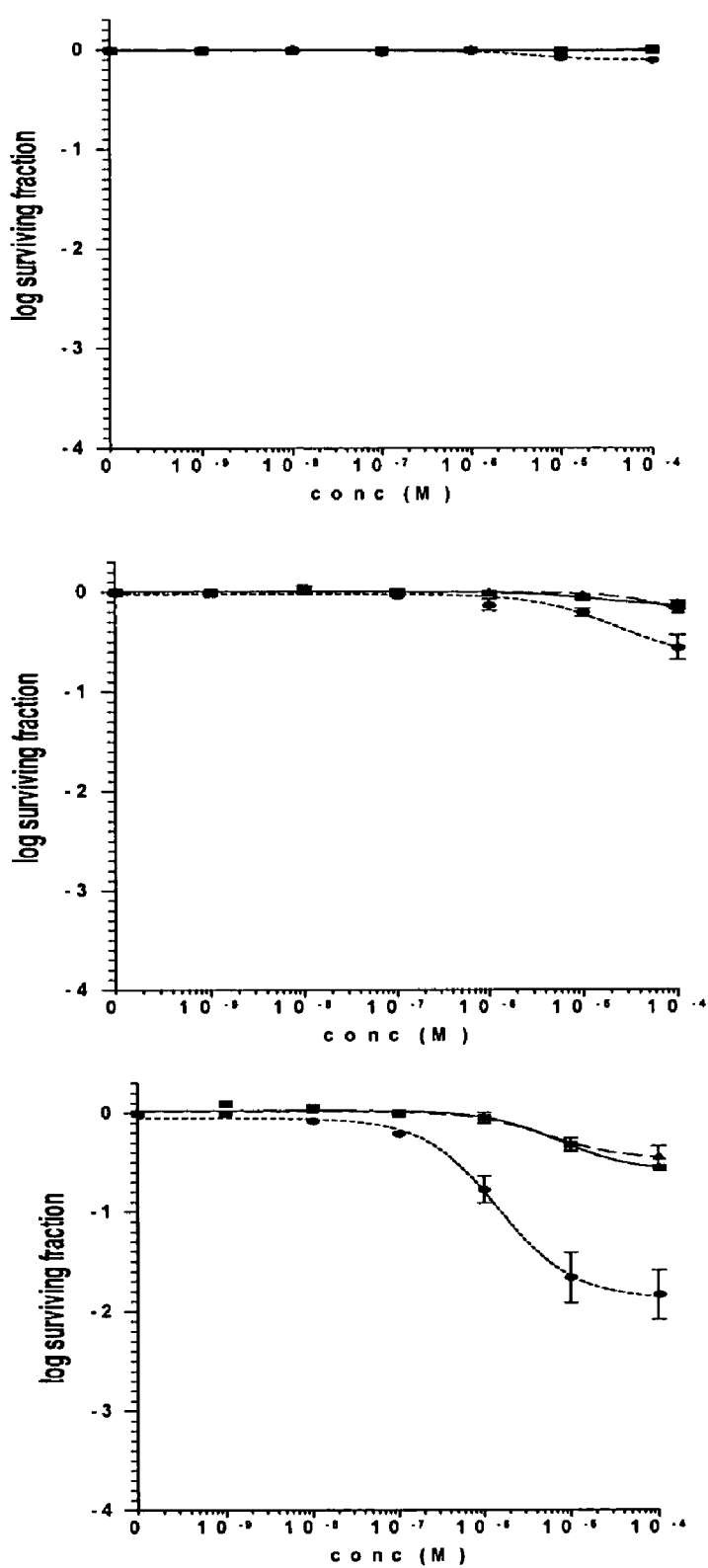
FIGS. 5 and 6 show clonogenic survival curves after 1, 4 and 24 hour timed exposures to KU0058684.
Figure 6:
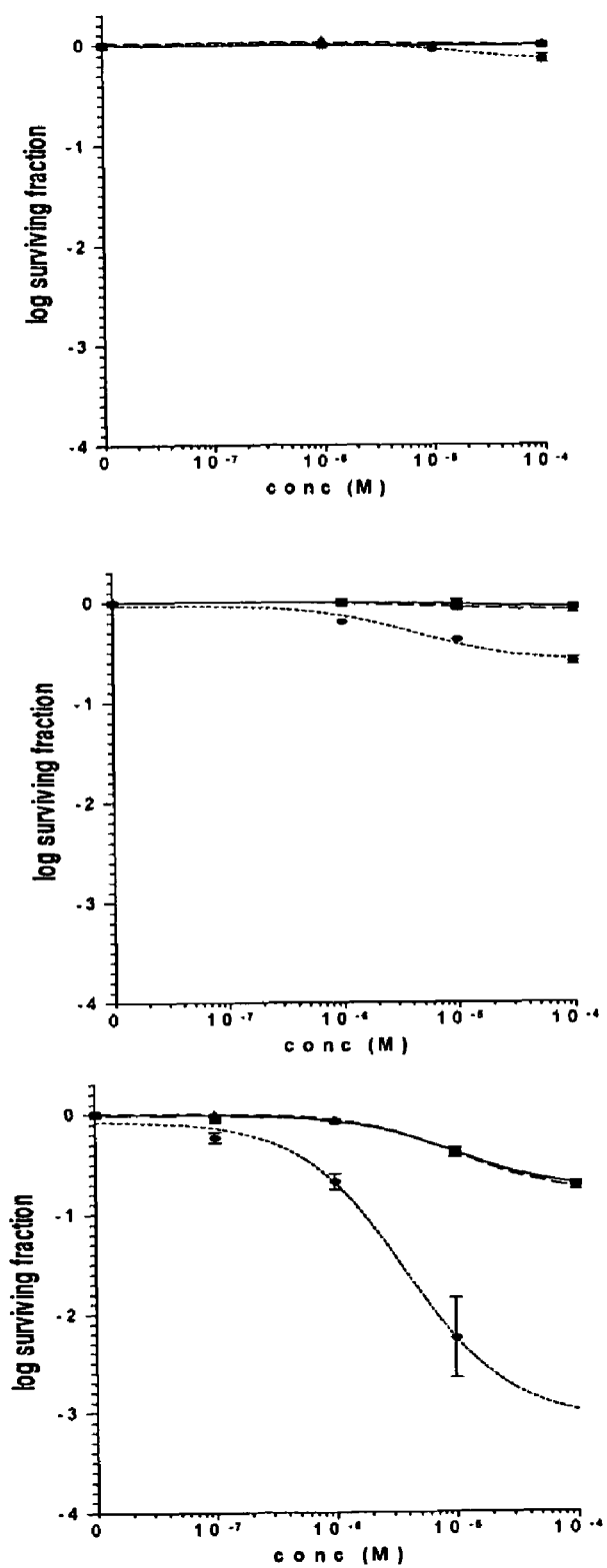

Time Course Dependence of the Effects on KU0058684 on Clonogenic Survival of Brca1 and Brca2 Deficient Cells Cells were exposed to different concentrations of KU0058684 for defined periods of time. The inhibitor was then removed and the effects measured using a clonogenic assay. The inhibitory effects of KU0058684 on clonal growth were apparent after a relatively short exposure time, 4 h, and were essentially complete by 24 h exposure (FIGS. 5 and 6). The effects of PARP inhibition were found to be irreversible as a short exposure followed by 10-14 days in the absence of the inhibitor prevents growth.

Effect of PARP Inhibition on Cell Cycle Arrest

Figure 7:
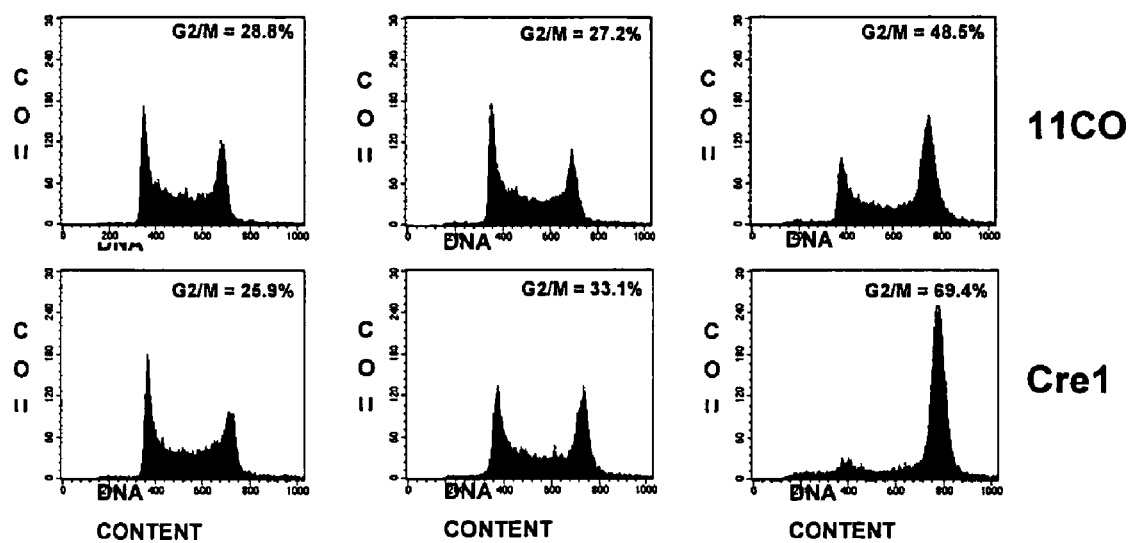
FIGS. 7 and 8 show that PARP inhibition in BRCA-1 and BRCA-2 mutant cells treated with PARP inhibitor resulted in enhanced G2/M arrest.
Figure 8:
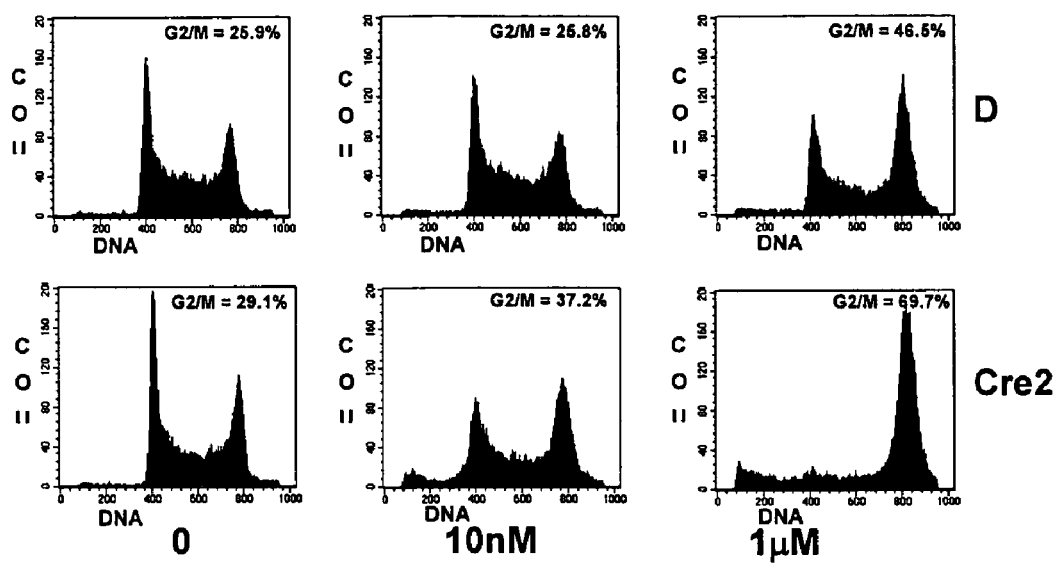
Figure 12:
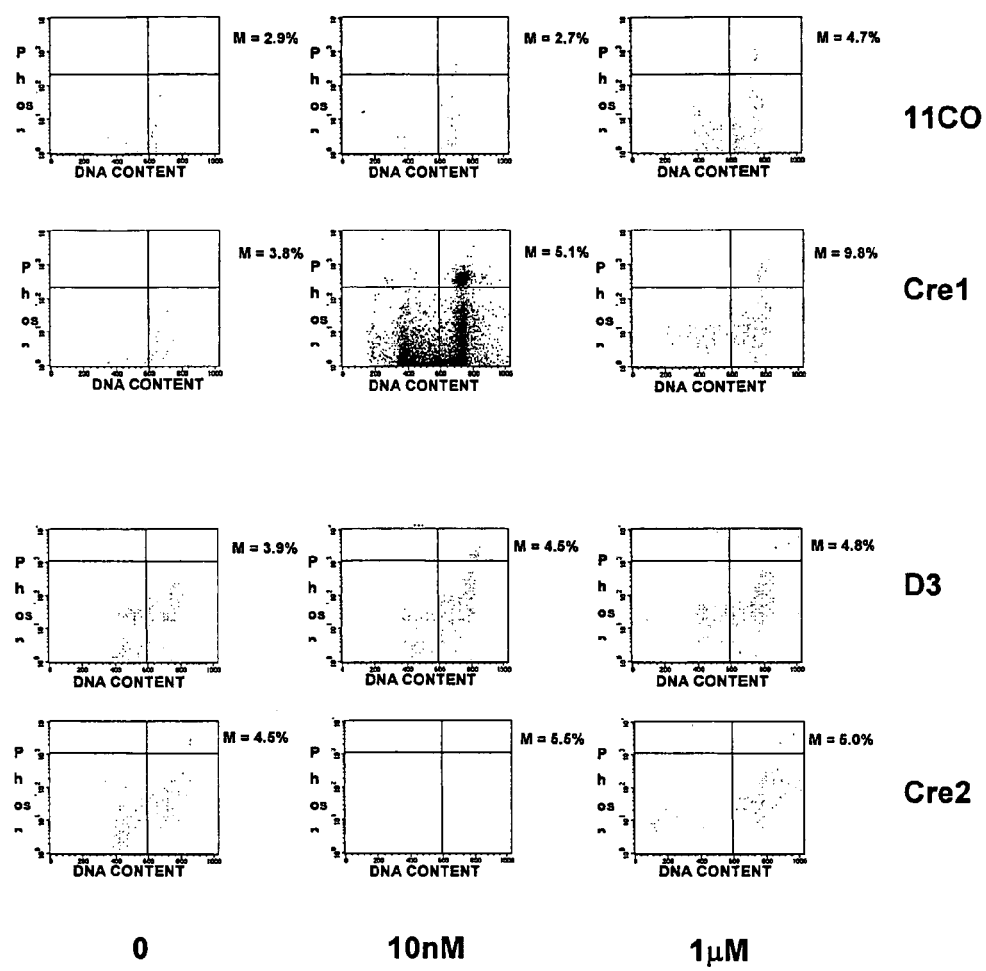
FIGS. 12 and 13 show phospho-histone H3 FACS data for ES cells
Figure 13:
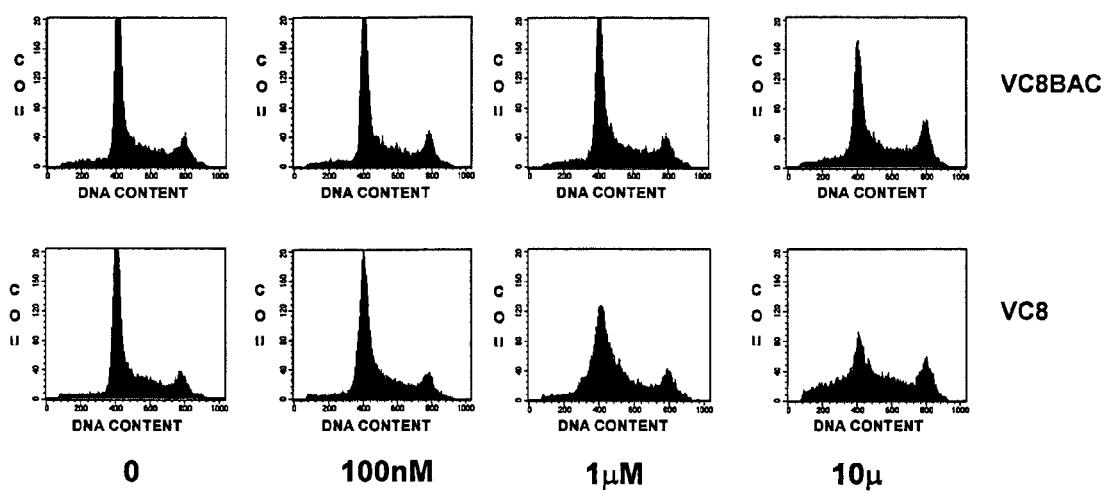

FACS analysis was used to determine whether PARP inhibition resulted in cell cycle arrest. Cells were exposed with KU0058684 for various periods then labelled with BrdU and the proportion of cells in each phase of the cell cycle. The results are shown in FIGS. 7 and 8. KU0058684 was observed to elicit a profound arrest of cells with a tetraploid DNA content indicating arrest in G$_2$ or M phase of the cell cycle. To further characterise this arrest, cells were analysed for both DNA content and for phosphorylated Histone H3, an M phase marker. To further characterise this arrest, cells were analysed for both DNA content and for phosphorylated Histone H3, an M phase marker (FIGS. 12 and 13). The majority of arrested cells did not label with anti-phospho histone H3 antibodies indicating that the majority of cells were arrested in G2.

Rad51 Foci Formation

One hallmark of Brca-dependent double-strand break repair is the formation of foci in the nucleus containing Rad51. The ability of KU0058684 to elicit Rad51 foci in wild-type and in Brca1 and Brca2 deficient cells was investigated.

Wild-type, and Brca1 and Brca2 defective ES cells were exposed to differing concentrations of KU0058684 for 48 hours. Cells were then fixed and stained for RAD51 foci as described by Tarsounas (Tarsounas M et al Oncogene. 2003 22(8):1115-23).

Figure 9:
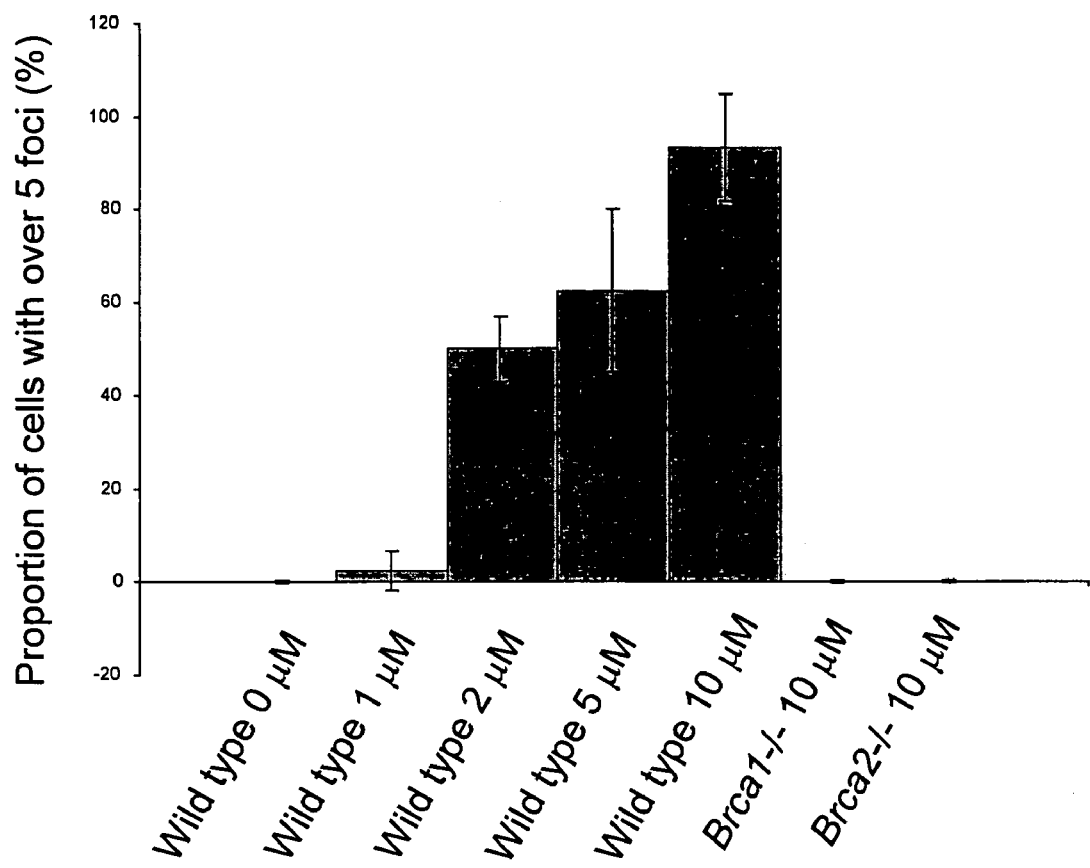
FIG. 9 shows a quantitative analysis of Rad51 foci formation induced by PARP inhibition in wild-type cells but not in Brca1 or Brca2 defective cells.

In wild-type ES cells, KU0058684 caused Rad51 foci formation in a dose-dependent fashion (FIG. 9). In contrast, no foci were induced in Brca1 or Brca2 deficient cells. This latter finding is consistent with previous observations that DNA damaging agents cannot cause Rad51 focus formation in Brca1 or Brca2 deficient cells.

KU0058684 is therefore shown to induce lesions, such as double-strand DNA breaks or lesions that degenerate into double-strand DNA breaks, which are repaired by a complex that involves Rad51 and which requires Brca1 and Brca2. Importantly, KU0051529 did not induce Rad51 focus formation at comparable doses, emphasizing the specificity of mechanism of sensitisation.

Comet Assays

Figure 10:
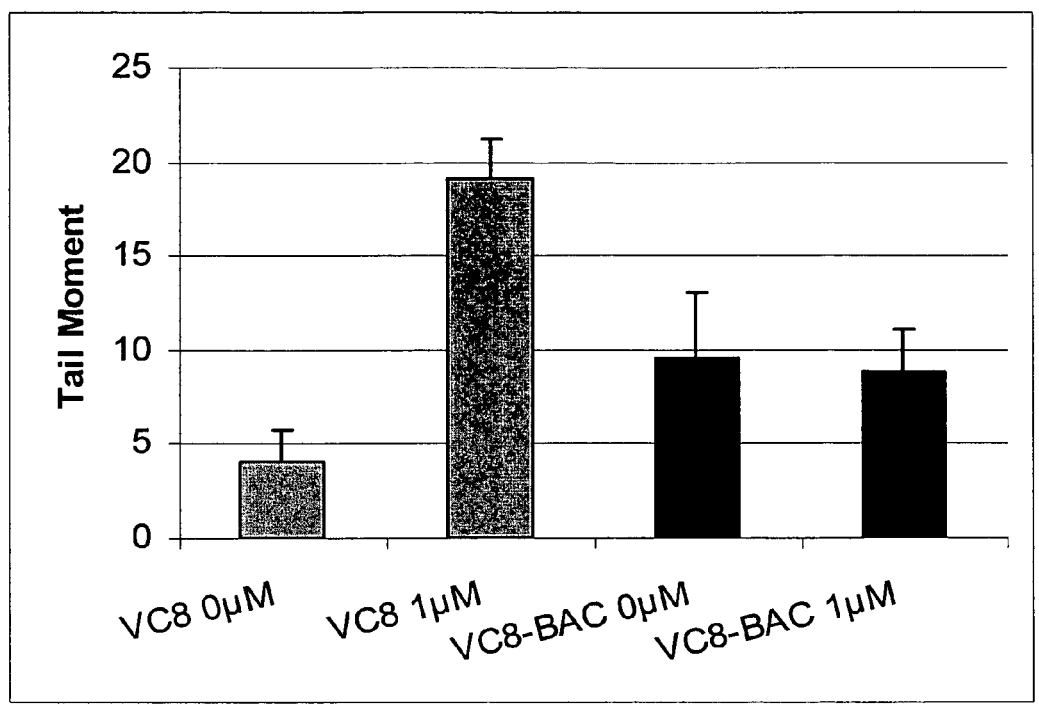
FIG. 10 shows a neutral comet analysis of BRCA2−/− VC8 and BRCA2 complemented VC8-BAC. KU0058684 (1 µM) treatment for 30 hours induces a significant increase in DNA DSBs as judged by an increase in tail moment in the BRCA2−/− cells whilst no significant increase in tail moment is observed in the BRCA2 complemented line. Average data from 3 independent experiments is shown +/− SEM, with 50 comets being scored for tail moment in each experiment.

To determine whether inhibition of PARP activity leads to the production of DNA double-strand breaks, neutral comet assays were performed on Brca2 mutant cells and their isogenic counterparts. The results are shown in FIG. 10. After a 30 hour exposure to 1 µM KU0058684, there was a 4.7 fold increase in the tail moment of the Brca2 deficient VC8 cells and no significant increase in tail moment for the complemented VC8-BAC line. This result shows that DNA double strand breaks induced by the PARPi are left unrepaired in the Brca2 deficient line.

Mitotic Chromosome Analysis

Examination of mitotic chromosomes of Brca1 and Brca2 deficient cells revealed that KU0058684 treatment resulted in frequent major aberrations. These included chromatid breaks and tri-radial and quadri-radial chromosomes. These phenotypes provide indication of a failure to repair double-strand breaks by sister chromatid gene conversion and the elevated use of alternative error-prone pathways.

ES Cell Xenografts and Treatment with KU0058684

Isogenic and Brca2 deficient ES cell derived tumours (teratomas) were produced in athymic BALB/c nude (nu/nu) mice as described above. The effect of KU0058684 on the growth of wild-type and Brca2 deficient xenograft tumours was measured and the results shown in FIG. 16.

KU0058684 was observed to dramatically reduce the growth of Brca2 deficient tumours relative to wild-type tumours.

Effect of PARP Inhibition in BRCA1 Cell-Deficient Lines

The MCF7-scrambled and MCF7-3.23 cell lines were produced as described above. MCF7-3.23 was found to have 30% expression of BRCA1 compared to MCF7-scrambled.

Figure 17:
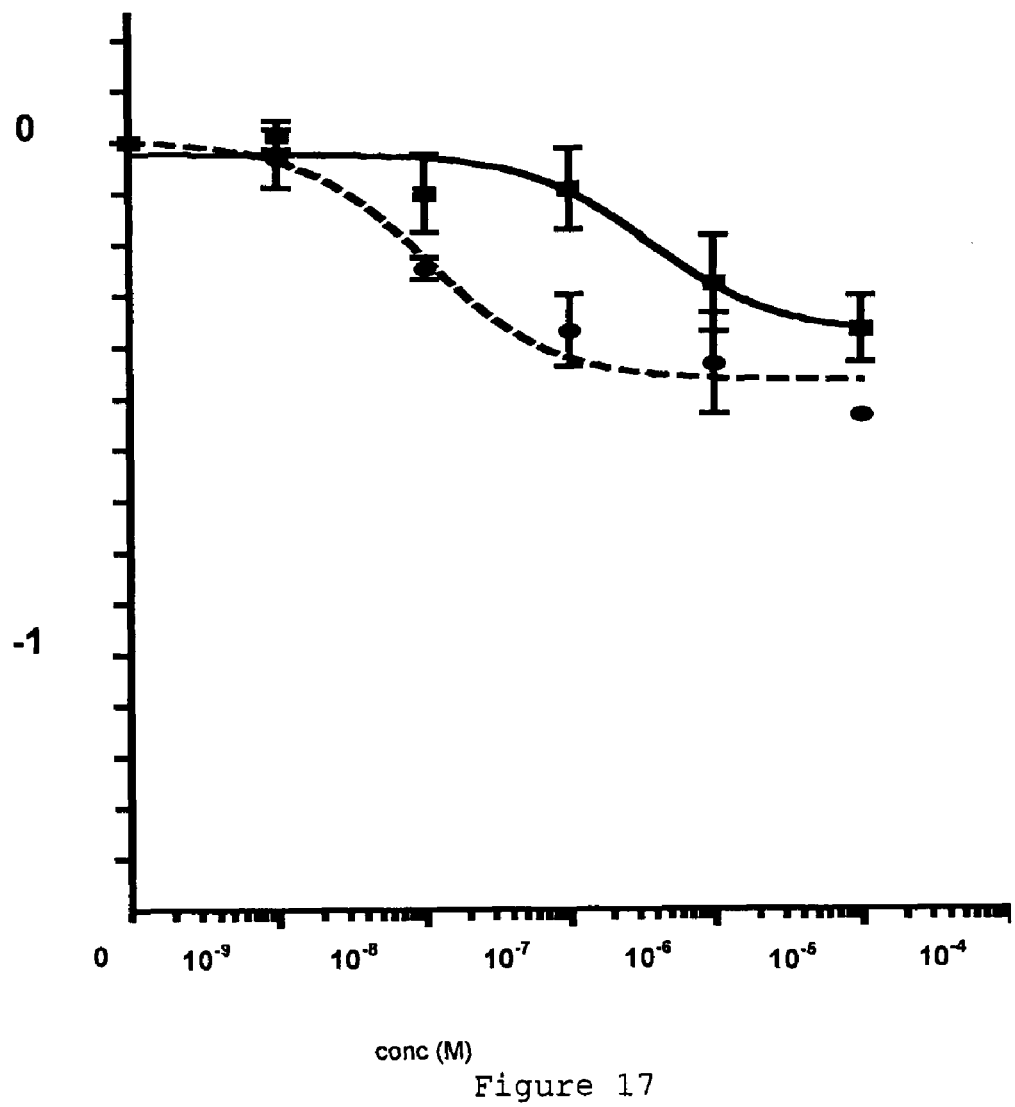
FIG. 17 shows clonal survival curves of BRCA1 wild-type (MCF7-scrambled) and BRCA1 silenced (MCF7-3.23) cells under continuous exposure to a range of concentrations of the PARP inhibitor KU0058684 for 12-14 days. Log concentration of inhibitor is plotted against log surviving fraction of cells. Error bars represent standard errors of the mean.
Figure 18:
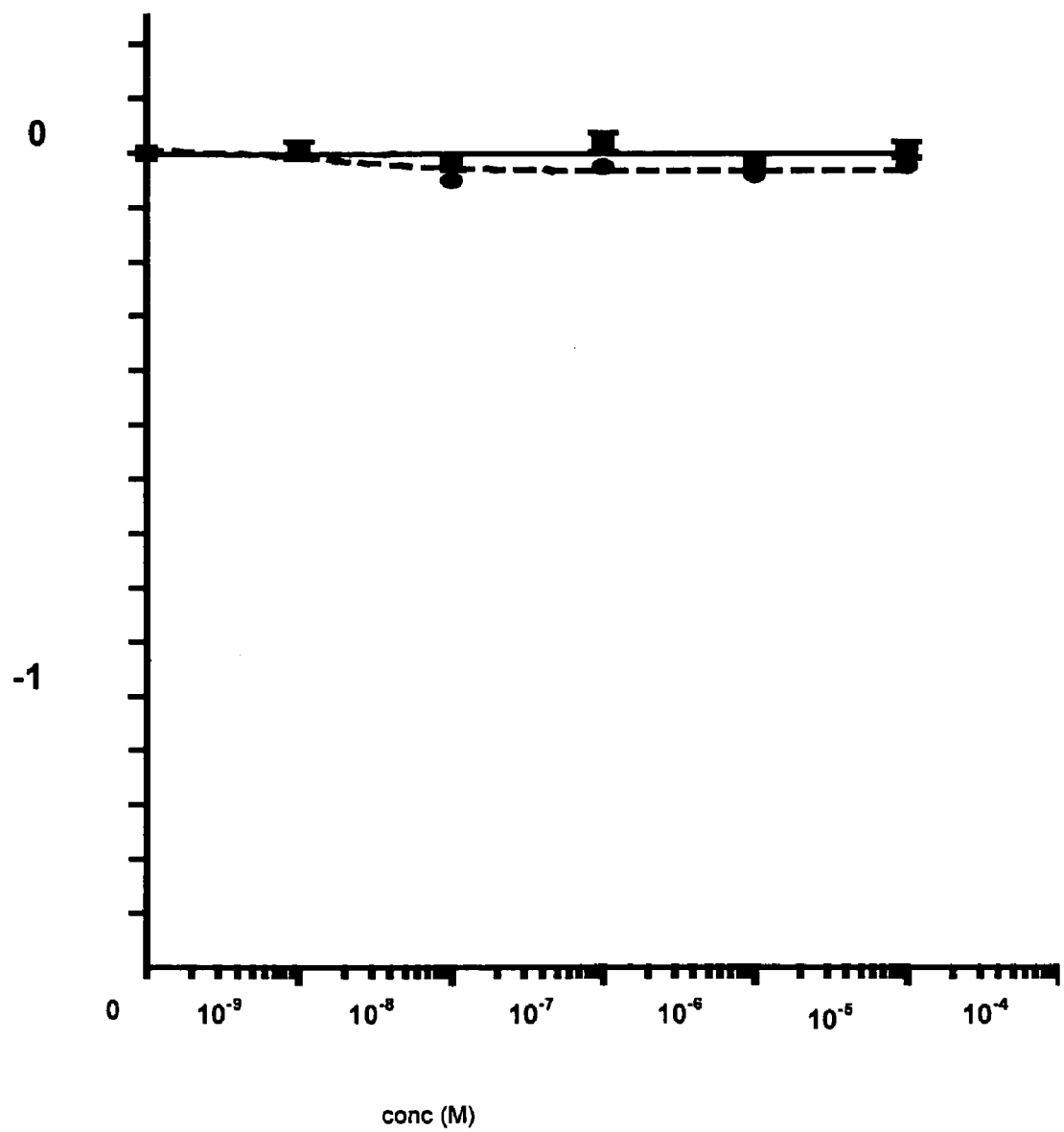
FIG. 18 shows clonal survival curves of BRCA1 wild-type (MCF7-scrambled) and BRCA1 silenced (MCF7-3.23) cells under continuous exposure to a range of concentrations of PARP inhibitor KU0051529 for 12-14 days. Log concentration of inhibitor is plotted against log surviving fraction of cells. Error bars represent standard errors of the mean.

Both MCF7-scrambled and MCF7-3.23 cells were treated with KU0058684 and KU0051529 and the survival of cells determined (FIGS. 17 and 18). KU0058684 is a potent PARP inhibitor whereas KU0051529 is less effective.

Neither MCF7-scrambled nor MCF7-3.23 cells displayed significant sensitivity to KU0051529 (FIG. 18). However both cell lines were sensitive to KU0058684.

MCF7-3.23 cells were shown to be significantly more sensitive to KU0058684 than MCF7-scrambled cells.

Interaction of PARP with the HR Dependent DNA DSB Pathway

Figure 11:
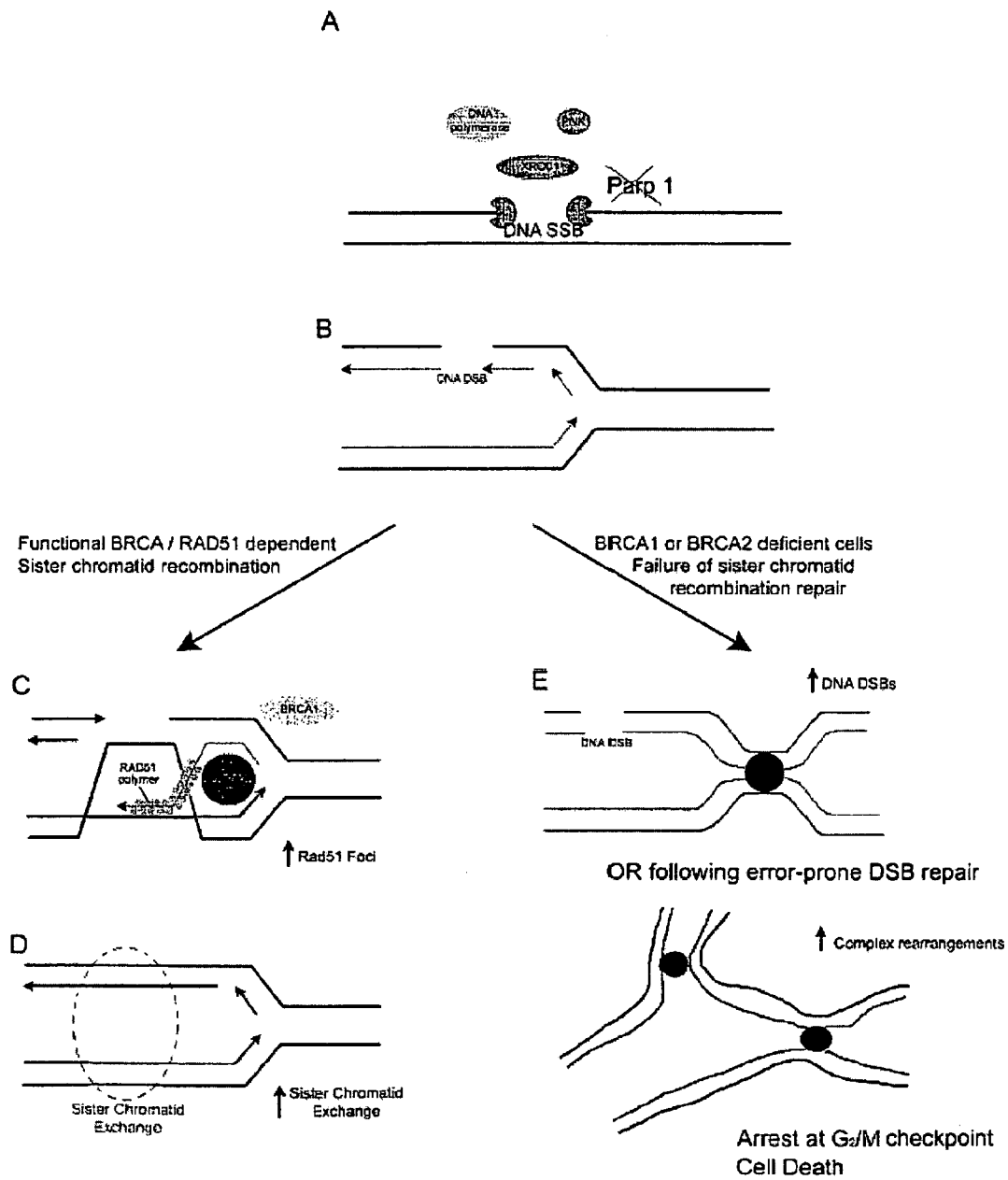
FIGS. 11A-D shows a possible model for the selective effects of PARP inhibition on BRCA1 and BRCA2 mutant cells.

Without limiting the scope of the invention in any way, one possible model for interaction between PARP and the HR dependent DNA DSB pathway is shown in FIG. 11.

DNA single-strand breaks (SSB) form due to oxidative damage and its repair. Inhibition of Parp-1 PAR polymerase activity prevents the recruitment of the XRCC1 scaffold protein and subsequent SSB gap filling by DNA polymerises (FIG. 11A).

Large numbers of SSBs persist and are encountered by DNA replication forks. The absence of a template strand at the SSB leads to a DSB and may, dependent on position, cause replication fork collapse (FIG. 11B).

The proximity of an undamaged sister chromatid template allows the invasion of the sister chromatid by RAD51 coated single stranded DNA filament and initiation of sister chromatid recombination repair. This process is dependent on BRCA1 and BRCA2 and is associated with the formation of multiple nuclear foci of RAD51. Collapsed replication forks can be restarted by a similar mechanism (FIG. 11C).

When Holliday junctions at recombination intermediates are resolved, a sister chromatid exchange (SCE) may occur. The excess number of SSBs encountered by replication forks during Parp-1 inhibition leads to an increase in SCEs (FIG. 11D).

In the absence of functional BRCA1 or BRCA2, RAD51 focus formation and sister chromatid recombination are severely impaired. The excess unrepaired SSBs form DNA DSBs during DNA replication but sister chromatid recombination does not occur. They remain unrepaired as chromatid breaks or are repaired by error prone RAD51 independent mechanisms causing complex chromosome rearrangements. These cells arrest when they encounter the G2/M DNA damage checkpoint and permanently arrest or apoptose (FIG. 11E).

RNAi data provided herein, along with the observation that KU0051529 was ineffective, demonstrate that PARP inhibition is responsible for the sensitisation effects observed.

PARP inhibition induces lesions that are normally repaired by sister chromatid exchange (SCE) (Wang Z Q, et al (1997) Genes Dev. Vol. 11(18):2347-58 and 'From DNA damage and stress signalling to cell death' G. de Murcia and S. Shall eds. Oxford University Press (2000)). PARP inhibition is known to increase SCE, with no concomitant increase in gene conversion of DSBs and therefore no global increase in the Rad51-dependent recombination pathway (Schultz N et al 2003, Nucleic Acids Research; vol. 31 (17): 4959-4964).

The synthetic lethality approach described herein may be useful both in the treatment of a) in tumours in BRCA carriers b) in tumours where other components of HR dependent DNA DSB repair are defective.

Although differences have been described in the age of onset and pathology of tumours in carriers of BRCA mutations, treatment is the same at present as for patients with sporadic disease. The present invention provides a new approach for these tumours is described herein.

Significantly, no heterozygous effect was observed. This is important for the therapeutic use of the described methods in heterozygous carriers of mutations in the HR dependent DNA DSB repair pathway, including, for example BRCA1/2 mutations.

What is claimed is:

1. A method of treatment of cancer in an individual comprising;
    identifying a cancer cell obtained from the individual as deficient in homologous recombination (HR) dependent deoxyribonucleic acid (DNA) double strand break (DSB) repair relative to normal cells; and
    administering a poly(ADP-ribose)polymerase (PARP) inhibitor to said individual.

2. A method according to claim 1 wherein said cancer is identified as a HR dependent DNA DSB repair deficient cancer by determining the HR dependent DNA DSB repair activity of cancer cells from the individual.

3. A method according to claim 1 wherein the activity of the HR dependent DNA DSB repair pathway is determined in the cancer cells by measuring the formation of foci containing Rad51 in the nucleus in response to DNA damage or PARP inhibitors.

4. A method according to claim 1 wherein said cancer is identified as an HR dependent DSB repair deficient cancer by determining the presence in cancer cells from the individual of one or more mutations or polymorphisms in a nucleic acid sequence encoding a component of the HR dependent DNA DSB repair pathway.

5. A method according claim 1 wherein said cancer comprises one or more cancer cells having a reduced or abrogated ability to repair DNA DSB by HR relative to normal cells.

6. A method according to claim 5 wherein said cancer cells are deficient in breast cancer 1 (BRCA1) or breast cancer 2 (BRCA2).

7. A method according to claim 6 wherein said cancer cells are homozygous for a mutation in BRCA1 or BRCA2.

8. A method according to claim 6 wherein said cancer cells are heterozygous for a mutation in BRCA1 and/or BRCA2.

9. A method according to claim 1 wherein said PARP inhibitor is a phthalazin-1(2H)-one.

10. A method according to claim 2 wherein the HR dependent DNA DSB repair activity of cancer cells from the individual is determined relative to normal cells.

11. A method according to claim 2 where the cancer cell obtained from the individual is deficient in a HR dependent DNA DSB repair pathway relative to normal cells.

* * * * *

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 1
gcggaguacg ccaagucca                                                19

<210> SEQ ID NO 2
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 2
caugccugau ccgcuaguc                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 3
ggaacctgtc tccacaaag                                                19

<210> SEQ ID NO 4
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 4
catgcctgat ccgctagtc                                                19
```